United States Patent
Ira et al.

(10) Patent No.: US 10,267,445 B2
(45) Date of Patent: *Apr. 23, 2019

(54) RELEASABLE VALVED COUPLER

(71) Applicant: Craig Alan Ira, Wichita, KS (US)

(72) Inventors: Craig A. Ira, Wichita, KS (US); Erin M. Wheeler, Denver, CO (US); Chene L. Cramer, Longmont, CO (US); Matthew Bauer, Vancouver, WA (US); David M. Browning, Portland, OR (US)

(73) Assignee: Craig Alan Ira, Wichita, KS (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/696,001

(22) Filed: Sep. 5, 2017

(65) Prior Publication Data

US 2017/0363240 A1 Dec. 21, 2017

Related U.S. Application Data

(63) Continuation of application No. 14/481,500, filed on Sep. 9, 2014, now Pat. No. 9,752,714, which is a
(Continued)

(51) Int. Cl.
*A61M 39/10* (2006.01)
*A61M 39/24* (2006.01)
(Continued)

(52) U.S. Cl.
CPC ............ *F16L 37/32* (2013.01); *A61M 39/26* (2013.01); *A61M 2039/1027* (2013.01);
(Continued)

(58) Field of Classification Search
CPC .............. F16L 37/32; A61M 39/26; A61M 2039/1027; A61M 2039/1094;
(Continued)

(56) References Cited

U.S. PATENT DOCUMENTS 115,917 A * 6/1871 Wharton ............... F16L 27/082
　　　　　　　　　　　　　　　　　　　285/921
198,402 A * 12/1877 Marsden ................... A47L 9/24
　　　　　　　　　　　　　　　　　　　285/921
(Continued)

OTHER PUBLICATIONS

PCT International Patent Application No. PCT/US2017/014189; International Search Report and Written Opinion of the International Searching Authority, dated May 23, 2017, 13 pages total.
(Continued)

*Primary Examiner* — Craig M Schneider
*Assistant Examiner* — Frederick D Soski
(74) *Attorney, Agent, or Firm* — Craig R. Miles; CR Miles P.C.

(57) ABSTRACT

A releasable valved coupler and a method of producing and using such a coupler including a coupler body having a first valve element and a coupler insert having a second valve element, wherein a first valve tip of the first valve element can engage a second valve tip of the second valve element upon insertion of the coupler insert inside of a tubular chamber of the coupler body, whereby the first valve element disengages a first valve seat and the second valve element disengages a second valve seat to open a flow path through the coupler. By moving the coupler body and the coupler insert in outward opposed axial directions, the first and second valve tips can disengage, correspondingly engaging the first valve element with the first valve seat and engaging the second valve element with the second valve seat to close the flow path through the coupler.

26 Claims, 13 Drawing Sheets

Related U.S. Application Data continuation-in-part of application No. 29/486,449, filed on Mar. 28, 2014, now Pat. No. Des. 746,447.

(51) Int. Cl.
  *F16L 37/32* (2006.01)
  *A61M 39/26* (2006.01)

(52) U.S. Cl.
  CPC ............ *A61M 2039/1094* (2013.01); *A61M 2039/2473* (2013.01); *Y10T 137/0519* (2015.04); *Y10T 137/87965* (2015.04)

(58) Field of Classification Search
  CPC ...... A61M 2039/2473; Y10T 137/0519; Y10T 137/87965; Y10T 137/87105; Y10T 137/87113; Y10T 137/87121; Y10T 137/7856
  USPC ........................................ 251/149.6; 285/921
  See application file for complete search history.

(56) References Cited

U.S. PATENT DOCUMENTS

| | | | |
|---|---|---|---|
| 921,691 | A * | 5/1909 | Friday ................ F16L 27/0828 |
| | | | 285/921 |
| 2,218,318 | A | 10/1940 | Pfauser |
| 2,444,888 | A * | 7/1948 | Baumgardner ......... A47L 9/242 |
| | | | 15/300.1 |
| 2,451,218 | A | 10/1948 | Hengst |
| 2,490,363 | A * | 12/1949 | Lang .................... F16L 37/133 |
| | | | 285/315 |
| 2,823,932 | A * | 2/1958 | Schigut ................ H02G 3/0616 |
| | | | 285/154.1 |
| 3,291,152 | A | 12/1966 | Comer |
| 3,460,801 | A | 8/1969 | Norton |
| 3,592,231 | A | 7/1971 | Lamb |
| 3,719,194 | A | 3/1973 | Anderson et al. |
| 3,916,929 | A | 11/1975 | Brown |
| 4,220,174 | A | 9/1980 | Spitz |
| 4,340,049 | A | 7/1982 | Munsch |
| 4,436,125 | A | 3/1984 | Blenkush |
| 4,500,118 | A | 2/1985 | Blenkush |
| 4,541,457 | A | 9/1985 | Blenkush |
| 4,630,847 | A | 12/1986 | Blenkush |
| 4,703,957 | A | 11/1987 | Blenkush |
| 4,733,692 | A | 3/1988 | Kotake et al. |
| 4,877,145 | A | 10/1989 | Manner |
| 4,903,995 | A | 2/1990 | Blenkush et al. |
| 4,934,655 | A | 6/1990 | Blenkush et al. |
| 4,946,200 | A | 8/1990 | Blenkush et al. |
| 5,009,252 | A | 4/1991 | Faughn |
| 5,033,777 | A | 7/1991 | Blenkush |
| 5,052,725 | A | 10/1991 | Meyer et al. |
| 5,076,615 | A | 12/1991 | Sampson |
| 5,104,158 | A | 4/1992 | Meyer et al. |
| 5,165,733 | A | 11/1992 | Sampson |
| 5,178,303 | A | 1/1993 | Blenkush et al. |
| D339,417 | S | 9/1993 | Sampson et al. |
| 5,257,833 | A * | 11/1993 | McNaughton ...... F16L 37/0987 |
| | | | 285/319 |
| 5,259,894 | A | 11/1993 | Sampson |
| 5,295,339 | A | 3/1994 | Manner |
| 5,316,041 | A | 5/1994 | Ramacier, Jr. et al. |
| 5,322,518 | A | 6/1994 | Schneider et al. |
| 5,353,836 | A | 10/1994 | deCler et al. |
| 5,390,702 | A | 2/1995 | Smith, III |
| 5,391,150 | A * | 2/1995 | Richmond ................. A61J 1/10 |
| | | | 604/111 |
| D357,307 | S | 4/1995 | Ramacier, Jr. et al. |
| 5,460,413 | A | 10/1995 | Sampson |
| 5,494,074 | A | 2/1996 | Ramacier, Jr. et al. |
| 5,529,085 | A | 6/1996 | Richards et al. |
| D372,093 | S | 7/1996 | Sampson et al. |
| D375,160 | S | 10/1996 | Sampson et al. |
| 5,564,752 | A | 10/1996 | Sampson |
| 5,639,064 | A | 6/1997 | deCler et al. |
| D384,731 | S | 10/1997 | Ramacier, Jr. et al. |
| 5,695,221 | A | 12/1997 | Sunderhaus |
| D388,876 | S | 1/1998 | Sampson |
| 5,704,106 | A | 1/1998 | Sampson et al. |
| 5,788,215 | A * | 8/1998 | Ryan .................... A61J 1/2096 |
| | | | 251/149.6 |
| 5,799,987 | A | 9/1998 | Sampson |
| 5,820,614 | A | 10/1998 | Erskine et al. |
| 5,826,610 | A | 10/1998 | Bodhaine |
| 5,845,943 | A | 12/1998 | Ramacier, Jr. et al. |
| 5,848,811 | A | 12/1998 | Sampson |
| 5,848,997 | A | 12/1998 | Erskine et al. |
| 5,869,803 | A | 2/1999 | Noguchi et al. |
| 5,911,403 | A | 6/1999 | deCler et al. |
| 5,937,885 | A | 8/1999 | Sampson |
| 5,938,244 | A | 8/1999 | Meyer |
| 5,975,489 | A | 11/1999 | deCler et al. |
| 6,024,124 | A | 2/2000 | Braun et al. |
| 6,082,401 | A | 7/2000 | Braun et al. |
| 6,095,191 | A | 8/2000 | Smith, III |
| 6,146,374 | A | 11/2000 | Erskine et al. |
| 6,161,578 | A | 12/2000 | Braun et al. |
| 6,206,040 | B1 | 3/2001 | Smith, III |
| 6,231,089 | B1 | 5/2001 | deCler et al. |
| 6,382,593 | B1 | 5/2002 | deCler et al. |
| 6,471,252 | B1 * | 10/2002 | Moretti ................ F16L 37/098 |
| | | | 285/305 |
| 6,626,419 | B2 | 9/2003 | deCler et al. |
| 6,649,829 | B2 | 11/2003 | Garber et al. |
| 6,692,040 | B1 | 2/2004 | McKay et al. |
| 6,705,591 | B2 | 3/2004 | deCler |
| 6,848,602 | B2 | 2/2005 | deCler et al. |
| 6,871,669 | B2 | 3/2005 | Meyer et al. |
| D503,778 | S | 4/2005 | Wicks |
| 6,897,374 | B2 | 5/2005 | Garber et al. |
| 6,902,144 | B2 | 6/2005 | deCler |
| 6,916,007 | B2 | 7/2005 | deCler et al. |
| 6,962,275 | B2 | 11/2005 | deCler et al. |
| 6,978,800 | B2 | 12/2005 | deCler et al. |
| 7,080,665 | B2 | 7/2006 | Whall |
| 7,163,022 | B2 | 1/2007 | Whall |
| 7,249,788 | B2 * | 7/2007 | Muhammad .......... F16L 37/092 |
| | | | 285/243 |
| 7,306,197 | B2 * | 12/2007 | Parrino ................. A61M 39/10 |
| | | | 251/149.6 |
| 7,394,375 | B2 | 7/2008 | Johnson |
| 7,434,842 | B2 | 10/2008 | Schmidt |
| 7,448,653 | B2 | 11/2008 | Jensen et al. |
| 7,469,472 | B2 | 12/2008 | deCler et al. |
| 7,488,446 | B2 | 2/2009 | Meyer et al. |
| 7,514,025 | B2 | 4/2009 | Hofmann et al. |
| 7,546,857 | B2 | 6/2009 | Chadbourne et al. |
| 7,547,047 | B2 | 6/2009 | deCler et al. |
| 7,562,906 | B2 | 7/2009 | Schmidt |
| D602,128 | S | 10/2009 | Williams et al. |
| 7,601,142 | B2 * | 10/2009 | House ................... A61M 39/12 |
| | | | 604/326 |
| 7,631,660 | B2 | 12/2009 | deCler et al. |
| 7,647,954 | B2 | 1/2010 | Garber et al. |
| 7,658,205 | B1 | 2/2010 | Edelman |
| D612,019 | S | 3/2010 | Williams et al. |
| D612,021 | S | 3/2010 | Schmidt |
| 7,695,020 | B2 | 4/2010 | Schmidt |
| 7,708,025 | B2 | 5/2010 | Johnson |
| 7,757,974 | B2 | 7/2010 | Hofmann et al. |
| 7,770,939 | B2 | 8/2010 | Jensen et al. |
| 7,806,139 | B2 | 10/2010 | Packham et al. |
| 7,841,357 | B2 | 11/2010 | Rankin |
| D629,894 | S | 12/2010 | Lombardi, III et al. |
| D630,320 | S | 1/2011 | Lombardi, III et al. |
| 7,875,346 | B2 | 1/2011 | Hofmann et al. |
| 7,878,553 | B2 | 2/2011 | Wicks et al. |
| D634,840 | S | 3/2011 | Lombardi, III et al. |
| D639,398 | S | 6/2011 | Wilhelm |
| 7,954,374 | B2 | 6/2011 | Rankin |
| 7,954,515 | B2 | 6/2011 | Gerst |
| D642,244 | S | 7/2011 | Wilhelm |

(56) References Cited

U.S. PATENT DOCUMENTS

| | | | |
|---|---|---|---|
| D645,547 S | 9/2011 | Lombardi et al. | |
| D649,240 S | 11/2011 | Lewis et al. | |
| D649,938 S | 12/2011 | Erickson et al. | |
| D649,939 S | 12/2011 | Erickson et al. | |
| D650,478 S | 12/2011 | Lewis | |
| D652,510 S | 1/2012 | Lombardi, III et al. | |
| D652,511 S | 1/2012 | Lombardi, III et al. | |
| D654,573 S | 2/2012 | Lombardi et al. | |
| 8,113,546 B2 | 2/2012 | Jensen et al. | |
| D655,393 S | 3/2012 | Whitaker | |
| 8,162,242 B2 | 4/2012 | Hofmann et al. | |
| D663,022 S | 7/2012 | Lombardi, III et al. | |
| 8,235,426 B2 | 8/2012 | Pisula, Jr. et al. | |
| 8,388,873 B2 | 3/2013 | Hofmann et al. | |
| 8,397,756 B2 | 3/2013 | Packham et al. | |
| 8,448,994 B2 | 5/2013 | Pisula, Jr. et al. | |
| RE44,310 E | 6/2013 | Chadbourne et al. | |
| 8,491,016 B2 | 7/2013 | Williams et al. | |
| 8,596,688 B2 | 12/2013 | Pisula, Jr. et al. | |
| D698,440 S | 1/2014 | Lombardi, III et al. | |
| D699,841 S | 2/2014 | Lombardi, III et al. | |
| 8,650,671 B1* | 2/2014 | Schuster | E03D 1/32 137/441 |
| 8,795,256 B1* | 8/2014 | Smith | A61M 39/26 604/249 |
| D712,537 S | 9/2014 | Lombardi et al. | |
| 8,897,756 B2 | 11/2014 | Skog et al. | |
| 8,945,091 B2 | 2/2015 | Williams et al. | |
| D724,703 S | 3/2015 | Downs | |
| 9,027,968 B2 | 5/2015 | Gerst | |
| 9,046,205 B2 | 6/2015 | Whitaker et al. | |
| 9,157,560 B2 | 10/2015 | Rehder et al. | |
| 9,186,494 B2* | 11/2015 | Fangrow | A61M 39/26 |
| 9,266,257 B2 | 2/2016 | Hofmann et al. | |
| 9,279,530 B2 | 3/2016 | Schmidt | |
| 9,283,344 B2* | 3/2016 | Sheffer | A61M 16/0816 |
| 9,364,653 B2 | 6/2016 | Williams et al. | |
| 9,371,921 B2 | 6/2016 | Whitaker | |
| D761,395 S | 7/2016 | Plackner et al. | |
| 9,388,929 B2 | 7/2016 | Lewis et al. | |
| D762,826 S | 8/2016 | Plackner et al. | |
| 9,464,741 B2 | 10/2016 | Lewis et al. | |
| 9,498,800 B2 | 11/2016 | Hofmann et al. | |
| 9,506,590 B2 | 11/2016 | Wilhelm et al. | |
| 9,752,714 B2* | 9/2017 | Ira | F16L 37/32 |
| 9,763,508 B2* | 9/2017 | Reishus | A45D 34/04 |
| 2001/0035220 A1 | 11/2001 | Russell | |
| 2002/0011730 A1 | 1/2002 | Stickan | |
| 2002/0014608 A1 | 2/2002 | deCler et al. | |
| 2002/0074533 A1 | 6/2002 | DeCler et al. | |
| 2002/0101076 A1 | 8/2002 | Barrier | |
| 2002/0129858 A1 | 9/2002 | Meyer et al. | |
| 2002/0170731 A1 | 11/2002 | Garber et al. | |
| 2002/0190453 A1 | 12/2002 | Wilhelm et al. | |
| 2003/0062498 A1 | 4/2003 | DeCler et al. | |
| 2003/0062501 A1 | 4/2003 | DeCler | |
| 2003/0196703 A1 | 10/2003 | DeCler et al. | |
| 2004/0130438 A1 | 7/2004 | Garber | |
| 2004/0169368 A1 | 9/2004 | Garber et al. | |
| 2004/0173769 A1 | 9/2004 | DeCler | |
| 2004/0222180 A1 | 11/2004 | Wicks et al. | |
| 2004/0232175 A1 | 11/2004 | DeCler et al. | |
| 2005/0001425 A1 | 1/2005 | DeCler et al. | |
| 2005/0012330 A1 | 1/2005 | Schmidt | |
| 2005/0057042 A1 | 3/2005 | Wicks | |
| 2005/0076964 A1 | 4/2005 | Whall | |
| 2005/0082828 A1 | 4/2005 | Wicks et al. | |
| 2005/0084410 A1 | 4/2005 | Meyer et al. | |
| 2005/0127117 A1 | 6/2005 | DeCler et al. | |
| 2005/0211934 A1 | 9/2005 | Garber et al. | |
| 2005/0237241 A1 | 10/2005 | Garber et al. | |
| 2005/0247371 A1 | 11/2005 | Chadbourne et al. | |
| 2006/0048849 A1 | 3/2006 | DeCler | |
| 2006/0076419 A1 | 4/2006 | Johnson | |
| 2006/0138704 A1 | 6/2006 | DeCler et al. | |
| 2006/0186233 A1 | 8/2006 | Holm et al. | |
| 2006/0196556 A1 | 9/2006 | Johnson | |
| 2006/0207345 A1 | 9/2006 | Rankin | |
| 2006/0231137 A1 | 10/2006 | Whall | |
| 2007/0001452 A1 | 1/2007 | Friel | |
| 2007/0025811 A1 | 2/2007 | Wilhelm | |
| 2007/0066965 A1* | 3/2007 | Coambs | A61M 39/26 604/533 |
| 2007/0169825 A1 | 7/2007 | Packham et al. | |
| 2007/0209716 A1 | 9/2007 | Rankin | |
| 2008/0011785 A1 | 1/2008 | Braun et al. | |
| 2008/0061553 A1 | 3/2008 | Schmidt | |
| 2008/0067807 A1 | 3/2008 | DeCler et al. | |
| 2008/0191069 A1 | 8/2008 | Hofmann et al. | |
| 2008/0277924 A1 | 11/2008 | Jensen et al. | |
| 2009/0188575 A1 | 7/2009 | Williams et al. | |
| 2009/0256355 A1 | 10/2009 | Wicks et al. | |
| 2009/0284007 A1 | 11/2009 | Schmidt | |
| 2010/0001516 A1 | 1/2010 | Pisula, Jr. et al. | |
| 2010/0006157 A1 | 1/2010 | Gerst | |
| 2010/0006162 A1 | 1/2010 | Rankin | |
| 2010/0019487 A1 | 1/2010 | deCler et al. | |
| 2010/0043988 A1 | 2/2010 | Hofmann et al. | |
| 2010/0155979 A1 | 6/2010 | Hofmann et al. | |
| 2010/0230950 A1 | 9/2010 | Williams et al. | |
| 2010/0295295 A1 | 11/2010 | Schmidt | |
| 2010/0301599 A1 | 12/2010 | Jensen et al. | |
| 2011/0012340 A1 | 1/2011 | Packham et al. | |
| 2011/0062701 A1 | 3/2011 | Downs et al. | |
| 2011/0121035 A1 | 5/2011 | Greter et al. | |
| 2011/0127767 A1 | 6/2011 | Wicks et al. | |
| 2011/0204621 A1 | 8/2011 | Whitaker et al. | |
| 2011/0204622 A1 | 8/2011 | Lewis et al. | |
| 2011/0210541 A1 | 9/2011 | Lewis et al. | |
| 2012/0031515 A1 | 2/2012 | Whitaker | |
| 2012/0068457 A1 | 3/2012 | Pisula, Jr. et al. | |
| 2012/0161051 A1 | 6/2012 | Williams et al. | |
| 2012/0179052 A1 | 7/2012 | Wilhelm et al. | |
| 2012/0259237 A1 | 10/2012 | Axelrod | |
| 2012/0286185 A1* | 11/2012 | Spolski | F16L 37/413 251/367 |
| 2013/0030387 A1 | 1/2013 | Williams et al. | |
| 2013/0092271 A1 | 4/2013 | Downs et al. | |
| 2013/0099489 A1 | 4/2013 | Williams et al. | |
| 2013/0207380 A1 | 8/2013 | Williams et al. | |
| 2013/0289517 A1 | 10/2013 | Williams et al. | |
| 2013/0333767 A1 | 12/2013 | Schmidt | |
| 2013/0334814 A1* | 12/2013 | Tiberghien | F16L 21/08 285/399 |
| 2014/0060675 A1 | 3/2014 | Wilhelm et al. | |
| 2014/0260554 A1 | 9/2014 | Rankin | |
| 2014/0261819 A1 | 9/2014 | Vranish | |
| 2015/0028586 A1 | 1/2015 | Gerst et al. | |
| 2015/0076815 A1 | 3/2015 | Lombardi, III et al. | |
| 2015/0090915 A1 | 4/2015 | Vranish | |
| 2015/0135502 A1 | 5/2015 | Rankin et al. | |
| 2015/0231369 A1 | 8/2015 | Gray et al. | |
| 2015/0260325 A1 | 9/2015 | Quick | |
| 2016/0018037 A1 | 1/2016 | Nichols et al. | |
| 2016/0033068 A1 | 2/2016 | Wilhelm | |
| 2016/0046130 A1 | 2/2016 | Burdge et al. | |
| 2016/0102791 A1 | 4/2016 | Johnson et al. | |
| 2016/0208971 A1 | 7/2016 | Lewis et al. | |
| 2016/0208972 A1 | 7/2016 | Lewis et al. | |
| 2016/0243348 A1 | 8/2016 | Williams et al. | |
| 2016/0305574 A1 | 10/2016 | Burdge | |
| 2017/0009919 A1 | 1/2017 | Lewis et al. | |

OTHER PUBLICATIONS

4salebyinventor.com. Break Away Valve for IV's. Website http://4salebyinventor.com, originally downloaded Jun. 20, 2014, 2 total pages.

Halkey-Roberts Corp. Robertsite Male Luer Valves. Trade show event, Booth 2139, Mar. 25, 2014, total 3 pages.

(56) References Cited

OTHER PUBLICATIONS

Design U.S. Appl. No. 29/486,449, filed Mar. 28, 2014.
U.S. Appl. No. 14/481,500, filed Sep. 9, 2014.

* cited by examiner

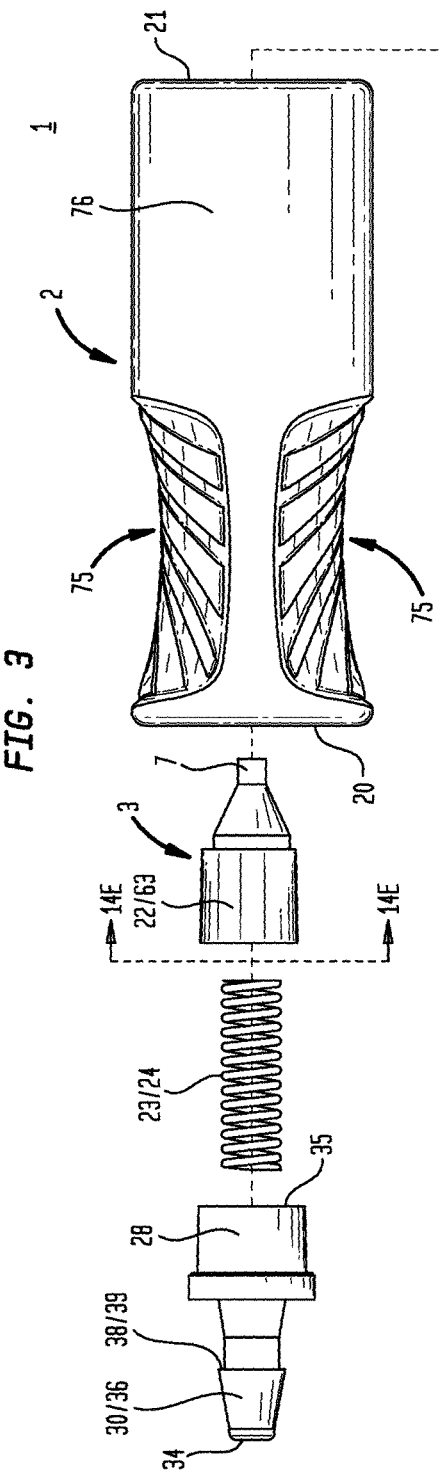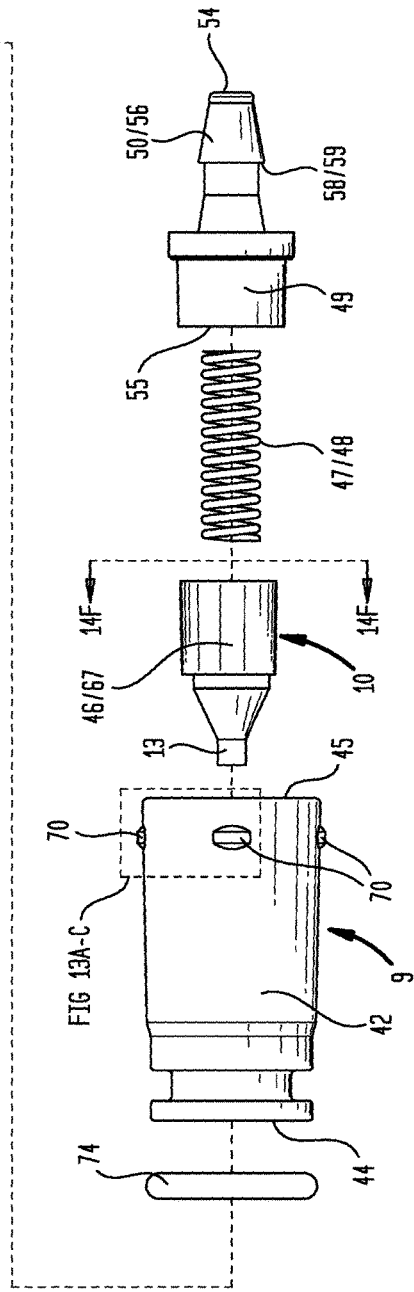
FIG. 3

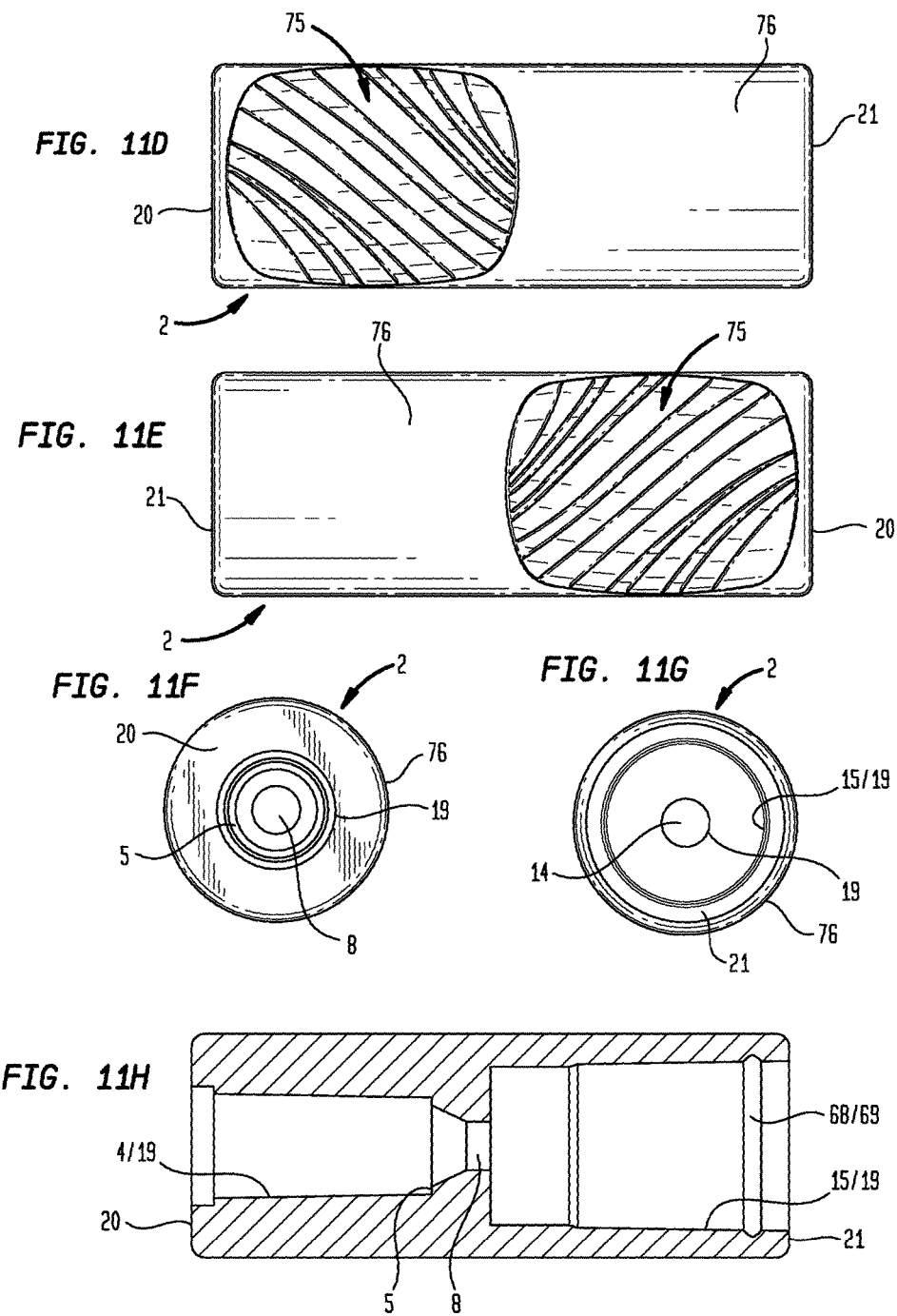

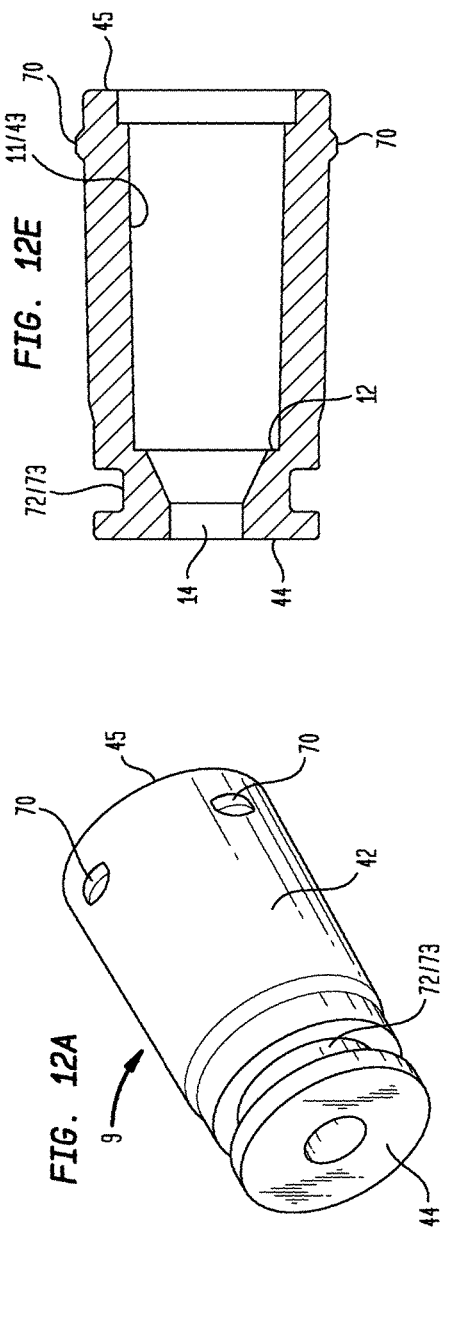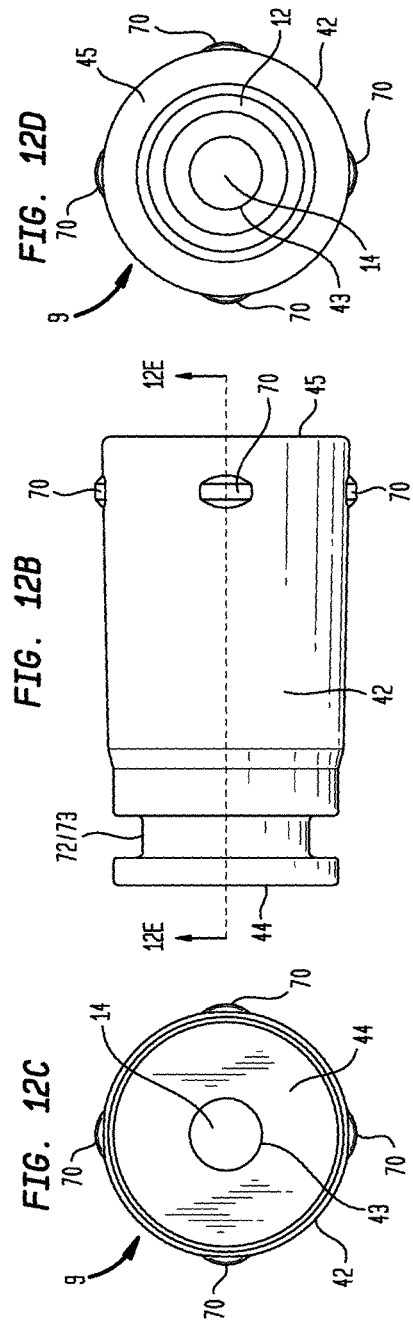

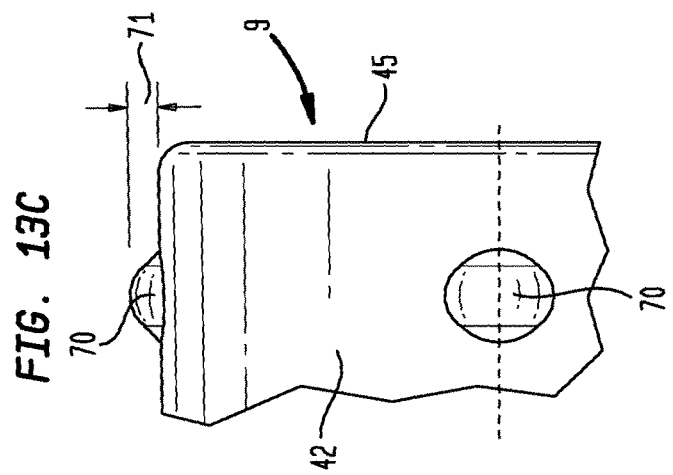
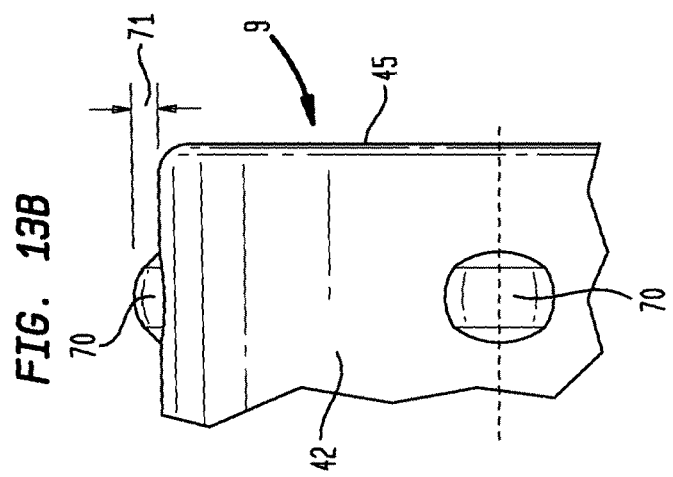
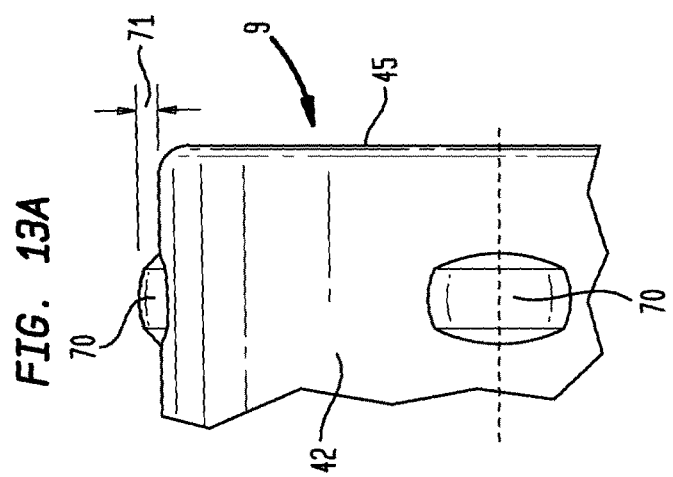

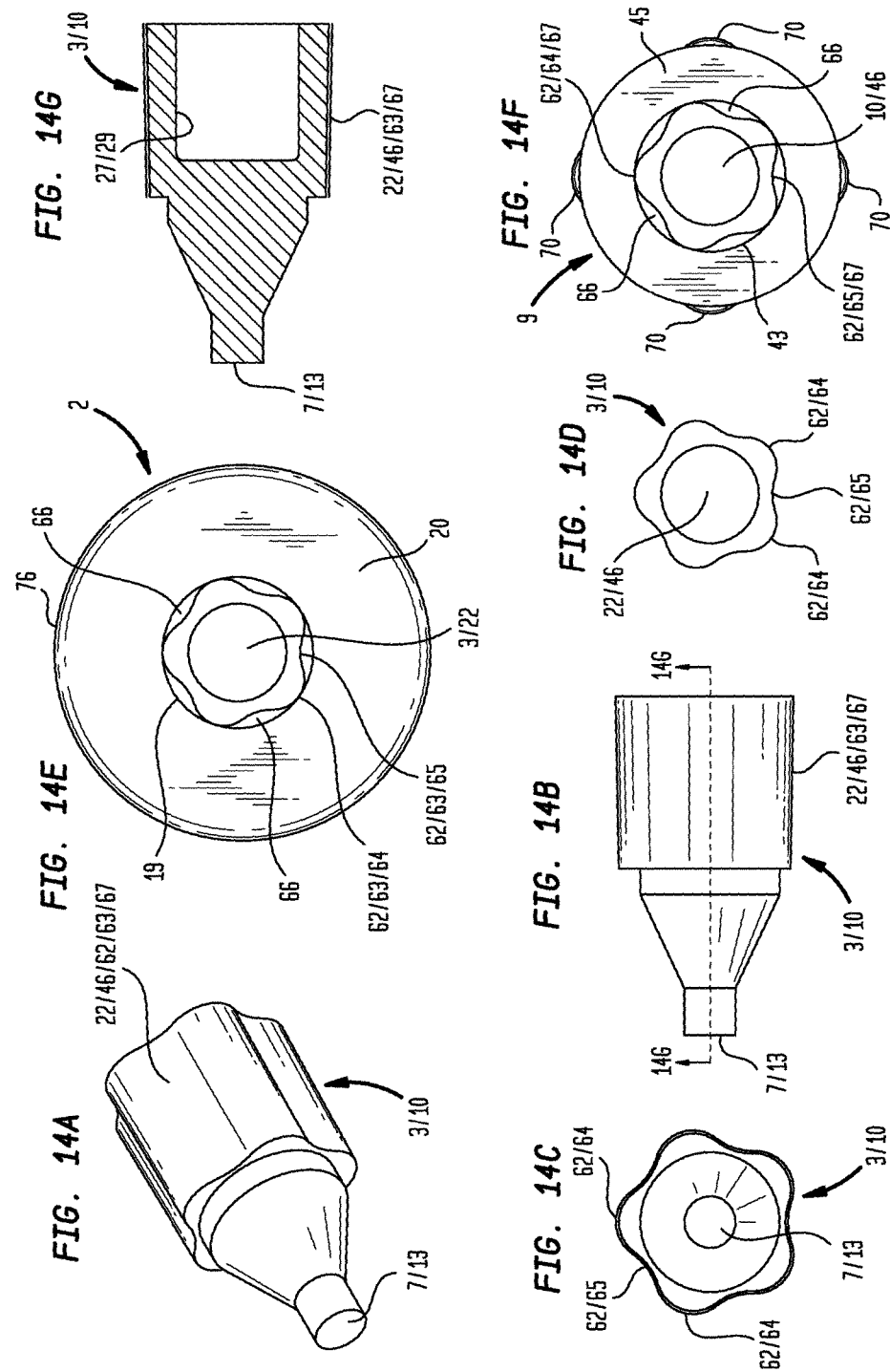

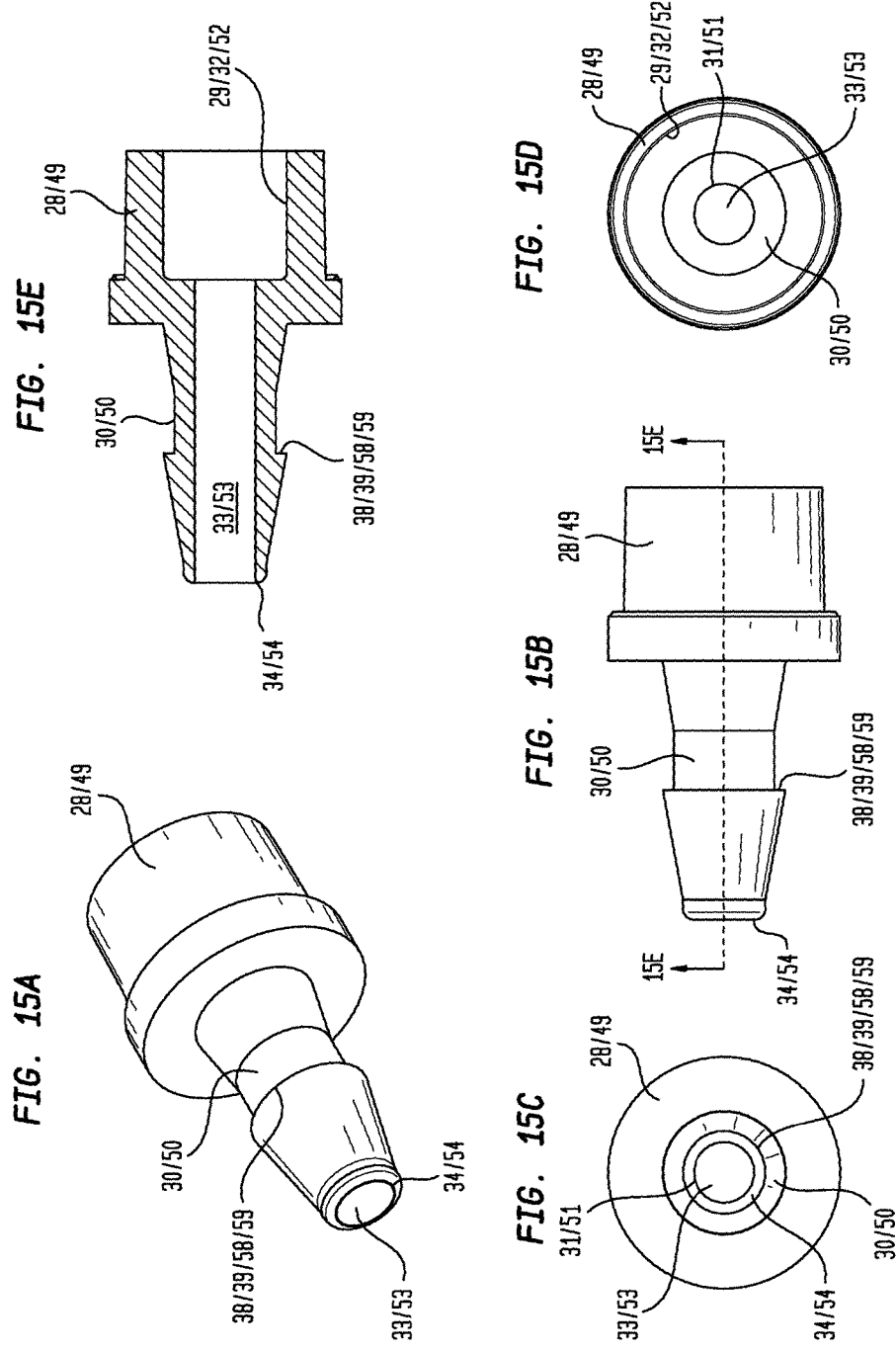

US 10,267,445 B2

RELEASABLE VALVED COUPLER

This United States Patent Application is a continuation of U.S. patent application Ser. No. 14/481,500, filed Sep. 9, 2014, now U.S. Pat. No. 9,752,714, issued Sep. 5, 2017, which is a continuation-in-part of U.S. Design patent application Ser. No. 29/486,449, filed Mar. 28, 2014, now U.S. Design Pat. No. D746447, issued Dec. 29, 2015, each hereby incorporated by reference herein.

I. BACKGROUND OF THE INVENTION

Conventional medical access devices employed for fluid infusion, including intravenous catheters, feeding tubes, or the like, may be unintentionally disengaged from either a fluid reservoir or a user. For example, an ambulatory user may inadvertently catch the fluid line on an object, disrupting the conventional medical access device and potentially causing damage to the fluid reservoir or trauma to the blood vessel or organ receiving the fluid infusion. Accordingly, a need exists for a coupler which can releasably couple a fluid line to a user.

II. SUMMARY OF THE INVENTION

A broad object of a particular embodiment of the invention can be to provide a coupler comprising a coupler body including a coupler body tubular internal surface which communicates between a coupler body first open end and a coupler body second open end, the coupler body tubular internal surface proximate the coupler body first open end defines a first valve guide coupled to a first valve seat having a first valve port, the first valve port communicating with a tubular chamber disposed proximate the coupler body second open end, a first valve element having a first valve body coupled to a first valve tip, the first valve element movable in the first valve guide to sealably engage the first valve seat in a closed position with the first valve tip extending through the first valve port a distance into the tubular chamber, a first valve actuator disposed adjacent the first valve element to facilitate movement of the first valve element toward the closed position, and a first tubular member coupled to a first tubular plug, the first tubular plug coupled to the first valve guide adjacent the first valve actuator, the first tubular member having a first tubular member external surface configured to join a first conduit; and a coupler insert including a coupler insert external surface configured to insert inside of the tubular chamber, a coupler insert tubular internal surface which communicates between a coupler insert first open end and a coupler insert second open end, the coupler insert tubular internal surface defining a second valve guide coupled to a second valve seat having a second valve port, the second valve port aligned with the first valve port upon insertion of the coupler insert inside of the tubular chamber, a second valve element having a second valve body coupled to a second valve tip, the second valve element movable in the second valve guide to sealably engage the second valve seat in a closed position with the second valve tip extending through the second valve port, a second valve actuator disposed adjacent the second valve element to facilitate movement of the second valve element toward the closed position, and a second tubular member coupled to a second tubular plug, the second tubular plug coupled to the second valve guide adjacent the second valve actuator, the second tubular member having a second tubular member external surface configured to join a second conduit; wherein the first valve tip engages the second valve tip upon insertion of the coupler insert inside of the tubular chamber, whereby the first valve element disengages the first valve seat and the second valve element disengages the second valve seat to open a flow path through the coupler.

Another broad object of a particular embodiment of the invention can be to provide a method of producing a coupler, the method comprising providing a coupler body including a coupler body tubular internal surface which communicates between a coupler body first open end and a coupler body second open end, the coupler body tubular internal surface proximate the coupler body first open end defines a first valve guide coupled to a first valve seat having a first valve port, the first valve port communicating with a tubular chamber disposed proximate the coupler body second open end; coupling a first valve element to the first valve guide, the first valve element having a first valve body coupled to a first valve tip, the first valve element movable in the first valve guide to sealably engage the first valve seat in a closed position with the first valve tip extending through the first valve port a distance into the tubular chamber; disposing a first valve actuator adjacent the first valve element to facilitate movement of the first valve element toward the closed position; coupling a first tubular plug to the first valve guide adjacent the first valve actuator; coupling a first tubular member to the first tubular plug, the first tubular member having a first tubular member external surface configured to join a first conduit; providing a coupler insert including a coupler insert external surface configured to insert inside of the tubular chamber and a coupler insert tubular internal surface which communicates between a coupler insert first open end and a coupler insert second open end, the coupler insert tubular internal surface defining a second valve guide coupled to a second valve seat having a second valve port, the second valve port aligned with the first valve port upon insertion of the coupler insert inside of the tubular chamber; coupling a second valve element to the second valve guide, the second valve element having a second valve body coupled to a second valve tip, the second valve element movable in the second valve guide to sealably engage the second valve seat in a closed position with the second valve tip extending through the second valve port; disposing a second valve actuator adjacent the second valve element to facilitate movement of the second valve element toward the closed position; coupling a second tubular plug to the second valve guide adjacent the second valve actuator; and coupling a second tubular member to the second tubular plug, the second tubular member having a second tubular member external surface configured to join a second conduit; wherein the first valve tip engages the second valve tip upon insertion of the coupler insert inside of the tubular chamber, whereby the first valve element disengages the first valve seat and the second valve element disengages the second valve seat to open a flow path through the coupler.

Another broad object of a particular embodiment of the invention can be to provide a method of using a coupler, the method including obtaining a coupler configured as described above, inserting the coupler insert inside of the tubular chamber, engaging the first valve tip with the second valve tip, and disengaging the first valve element from the first valve seat and disengaging the second valve element from the second valve seat to open a flow path through the coupler.

Another broad object of a particular embodiment of the invention can be to provide a method of using a coupler, the method further including moving the coupler body and the coupler insert in outward opposed axial directions, disengaging the first valve tip and the second valve tip, and engaging the first valve element with the first valve seat and engaging the second valve element with the second valve seat to close the flow path through the coupler.

Naturally, further objects of the invention are disclosed throughout other areas of the specification, drawings, and claims.

III. BRIEF DESCRIPTION OF THE DRAWINGS

FIG. 3 is an exploded view of a particular embodiment of the inventive coupler.

FIG. 11D is a first side view of a particular embodiment of a coupler body.

FIG. 11E is a second side view of a particular embodiment of a coupler body.

FIG. 11F is a first end view of a particular embodiment of a coupler body.

FIG. 11G is a second end view of a particular embodiment of a coupler body.

FIG. 11H is a cross-sectional view 11H-11H of the particular embodiment of the coupler body shown in FIG. 11B.

FIG. 12A is a perspective view of a particular embodiment of a coupler insert.

FIG. 12B is a view of a particular embodiment of a coupler insert.

FIG. 12C is a first end view of a particular embodiment of a coupler insert.

FIG. 12D is a second end view of a particular embodiment of a coupler insert.

FIG. 12E is a cross-sectional view 12E-12E of the particular embodiment of the coupler insert shown in FIG. 12B.

FIG. 13A is an enlarged top view of the particular embodiment of the coupler insert shown in FIG. 3.

FIG. 13B is an enlarged bottom view of the particular embodiment of the coupler insert shown in FIG. 3.

FIG. 13C is an enlarged bottom view of the particular embodiment of the coupler insert shown in FIG. 3.

FIG. 14A is a perspective view of a particular embodiment of a valve element.

FIG. 14B is a view of a particular embodiment of a valve element.

FIG. 14C is a first end view of a particular embodiment of a valve element.

FIG. 14D is a second end view of a particular embodiment of a valve element.

FIG. 14E is a cross-sectional view 14E-14E of the particular embodiment of the valve element shown in FIG. 3.

FIG. 14F is a cross-sectional view 14F-14F of the particular embodiment of the valve element shown in FIG. 3.

FIG. 14G is a cross-sectional view 14G-14G of the particular embodiment of the valve element shown in FIG. 14B.

FIG. 15A is a perspective view of a particular embodiment of a tubular member coupled to a tubular plug.

FIG. 15B is a view of a particular embodiment of a tubular member coupled to a tubular plug.

FIG. 15C is a first end view of a particular embodiment of a tubular member coupled to a tubular plug.

FIG. 15D is a second end view of a particular embodiment of a tubular member coupled to a tubular plug.

FIG. 15E is a cross-sectional view 15E-15E of the particular embodiment of the tubular member coupled to the tubular plug shown in FIG. 15B.

IV. DETAILED DESCRIPTION OF THE INVENTION

Figure 1:
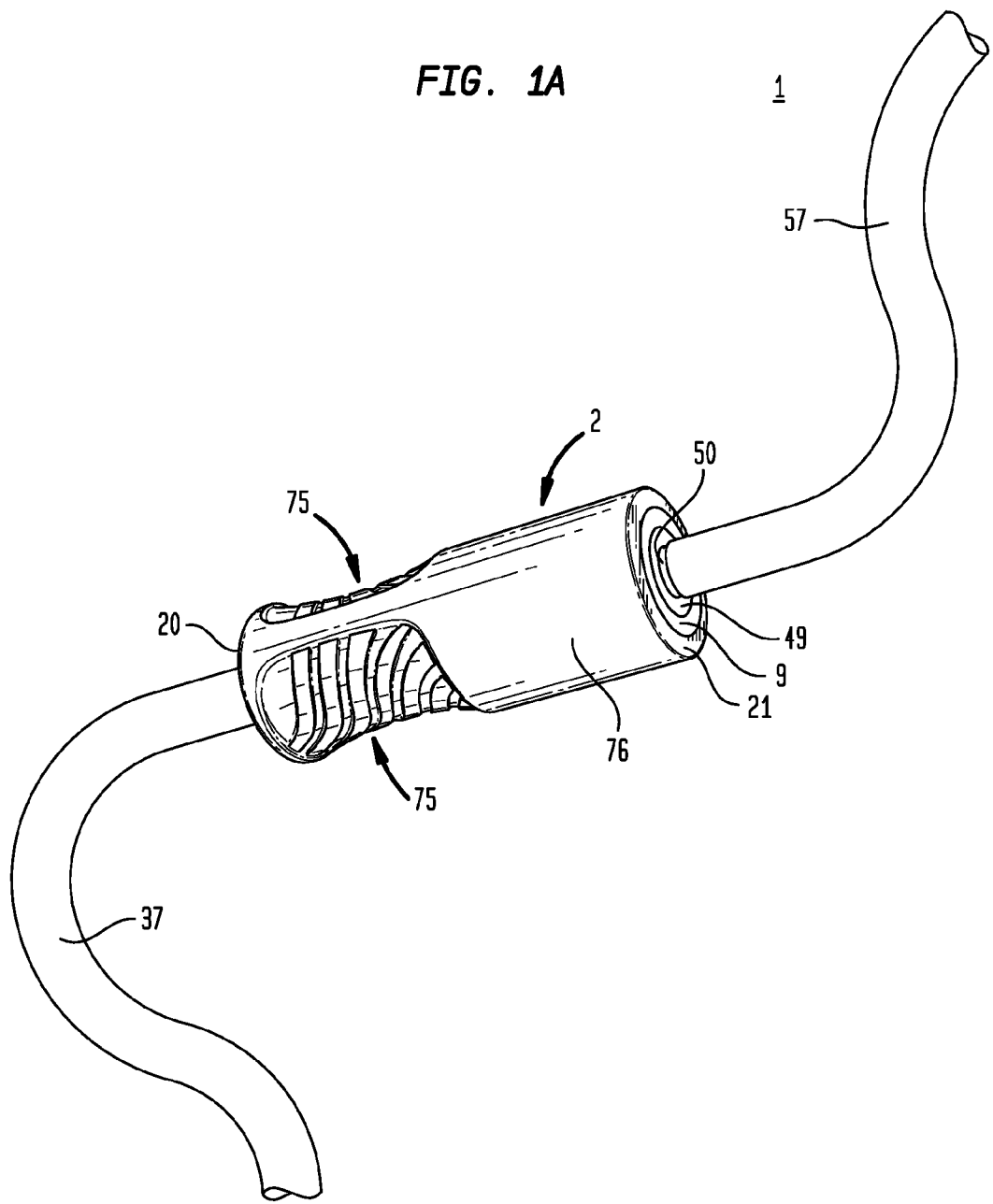
FIG. 1A is an illustration of a method of using a particular embodiment of the inventive coupler.
FIG. 1B is an illustration of a method of using a particular embodiment of the inventive coupler.
Figure 2:
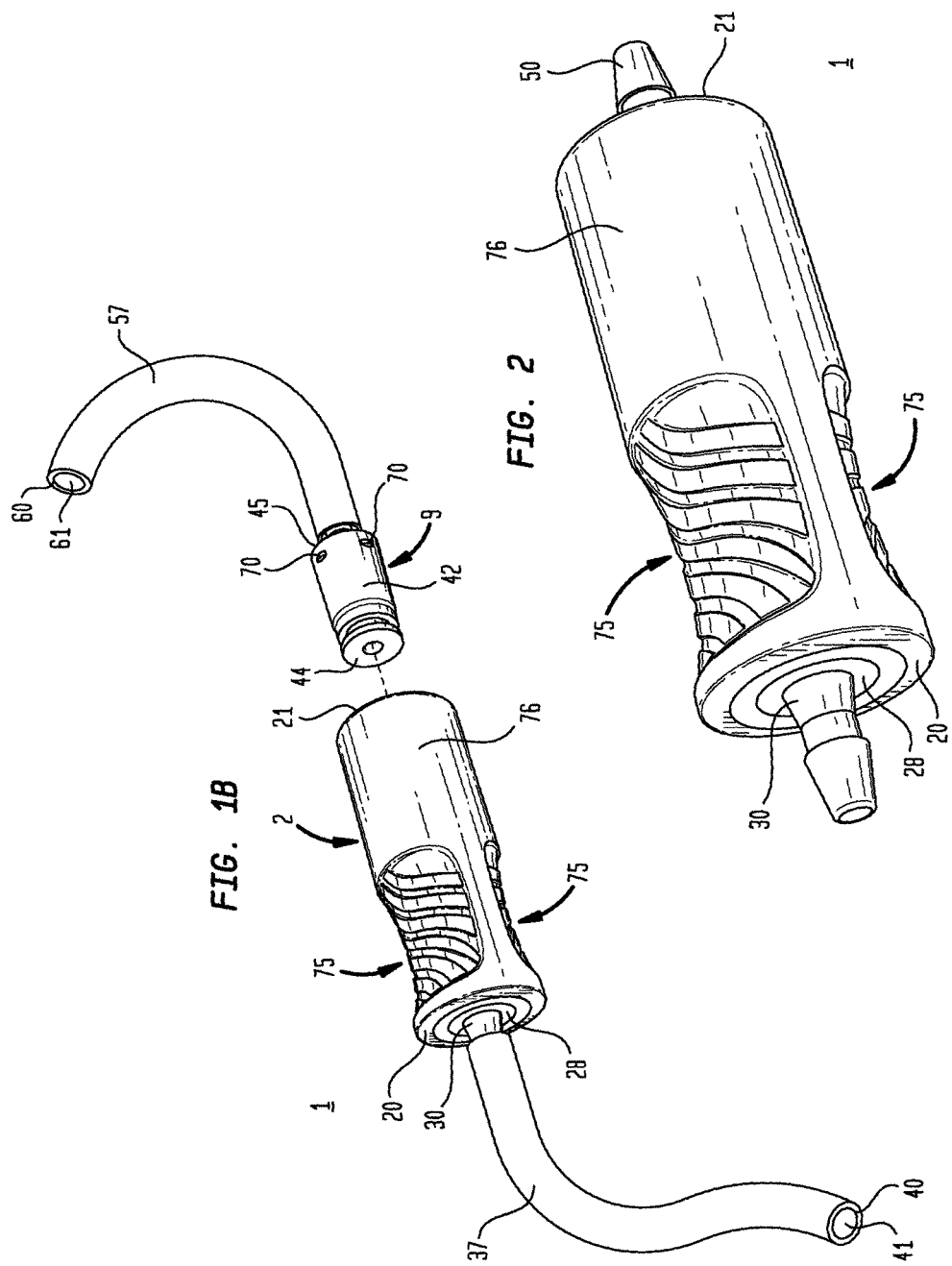
FIG. 2 is a perspective view of a particular embodiment of the inventive coupler.
Figure 4:
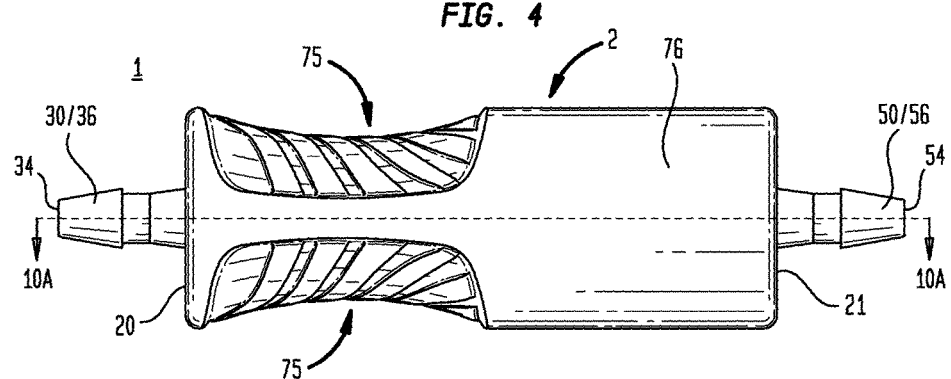
FIG. 4 is a top view of a particular embodiment of the inventive coupler.
Figure 5:
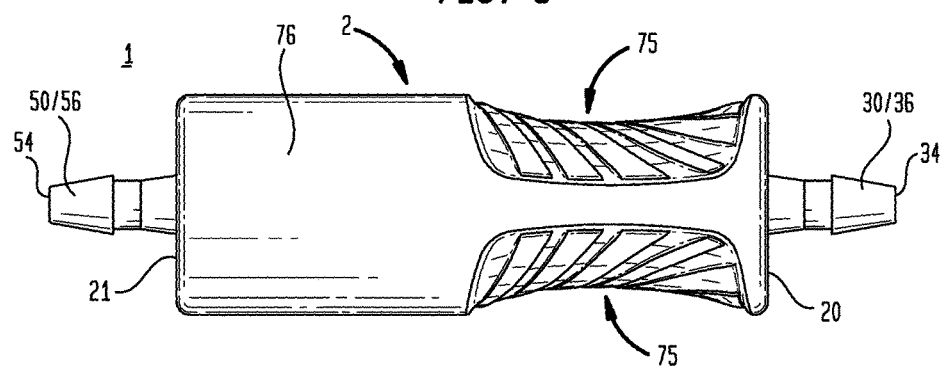
FIG. 5 is a bottom view of a particular embodiment of the inventive coupler.
Figure 6:
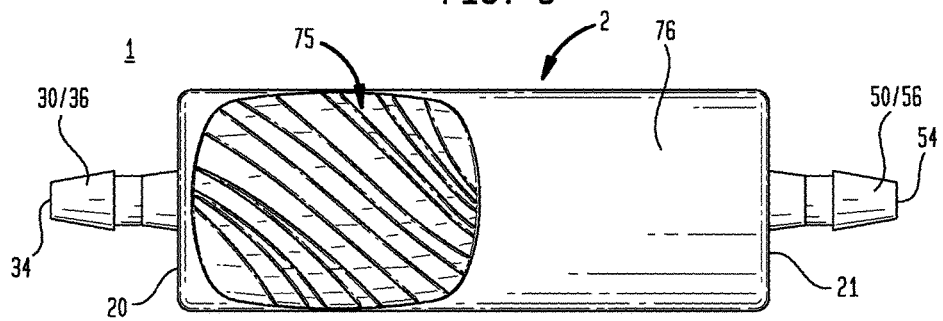
FIG. 6 is a first side view of a particular embodiment of the inventive coupler.
Figure 7:
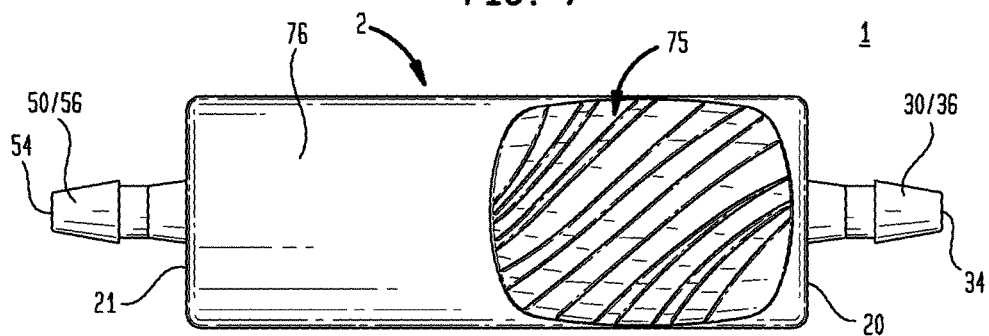
FIG. 7 is a second side view of a particular embodiment of the inventive coupler.
Figure 8:
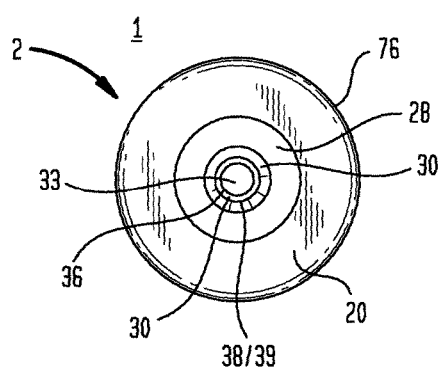
FIG. 8 is a first end view of a particular embodiment of the inventive coupler.
Figure 9:
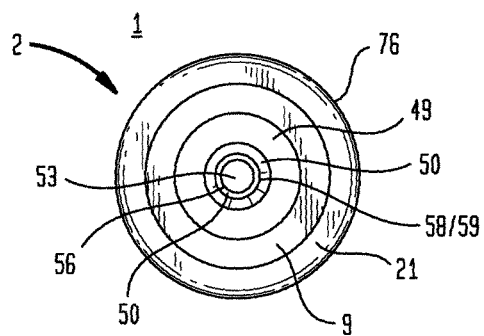
FIG. 9 is a second end view of a particular embodiment of the inventive coupler.

Now referring primarily to FIG. 1A, which illustrates a method of using a particular embodiment of an inventive coupler (1) including a coupler body (2) having a first valve element (3) movable in a first valve guide (4) to sealably engage a first valve seat (5) in a closed position (6) with a first valve tip (7) extending outward of a first valve port (8) and a coupler insert (9) having a second valve element (10) movable in a second valve guide (11) to sealably engage a second valve seat (12) in a closed position (6) with a second valve tip (13) extending outward of a second valve port (14). By inserting the coupler insert (9) into a tubular chamber (15) of the coupler body (2), the first and second valve elements (3)(10) can be substantially coaxially aligned disposing the first valve tip (7) adjacent the second valve tip (13). Further inward opposed axial movement of the coupler insert (9) within the tubular chamber (15) of the coupler body (2) generates corresponding inward opposed axial movement of the first and second valve tips (7)(13), disposing the first valve port (8) in substantially coaxial adjacent relation with the second valve port (14), concurrently disengaging the first valve element (3) from the first valve seat (5) and disengaging the second valve element (10) from the second valve seat (12), thereby disposing the first and second valve elements (3)(10) in an open position (16) initiating fluid flow (17) through the flow path (18) of the inventive coupler (1).

Now referring primarily to FIG. 1B, by moving the coupler body (2) and the coupler insert (9) in outward opposed axial directions, the coupler insert (9) can be removed from within the tubular chamber (15) of the coupler body (2). Concurrently, the first valve tip (7) can disengage the second valve tip (13) sealably engaging the first and second valve elements (3)(10) with the corresponding first and second valve seats (5)(12), positioning the first and second valve elements (3)(10) in the closed position (6), thereby interrupting the fluid flow (17) through the flow path (18) of the inventive coupler (1).

Figure 10A:
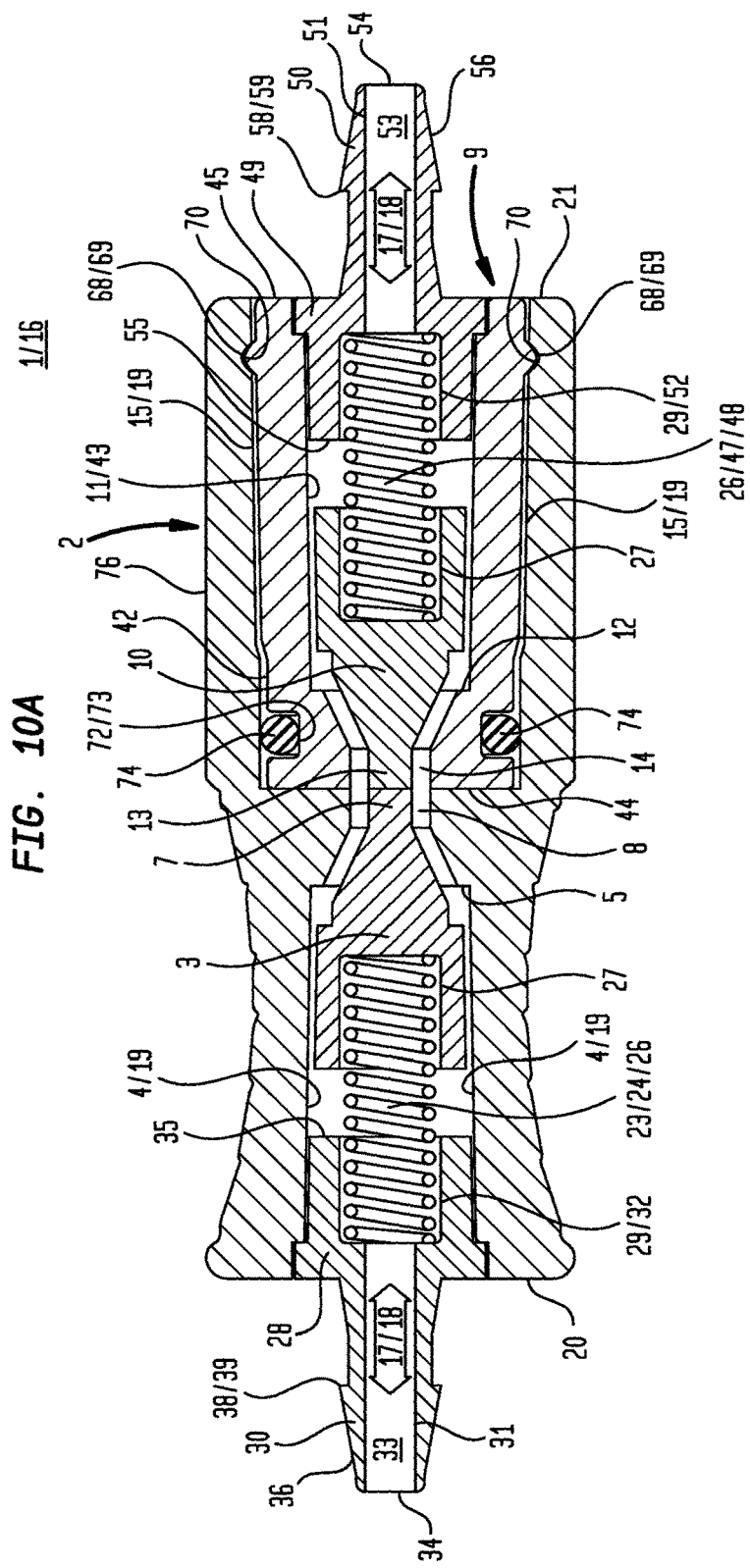
FIG. 10A is a cross-sectional view 10A-10A of the particular embodiment of the inventive coupler shown in FIG. 4, wherein a first valve element and a second valve element are positioned in an open position.
Figure 10B:
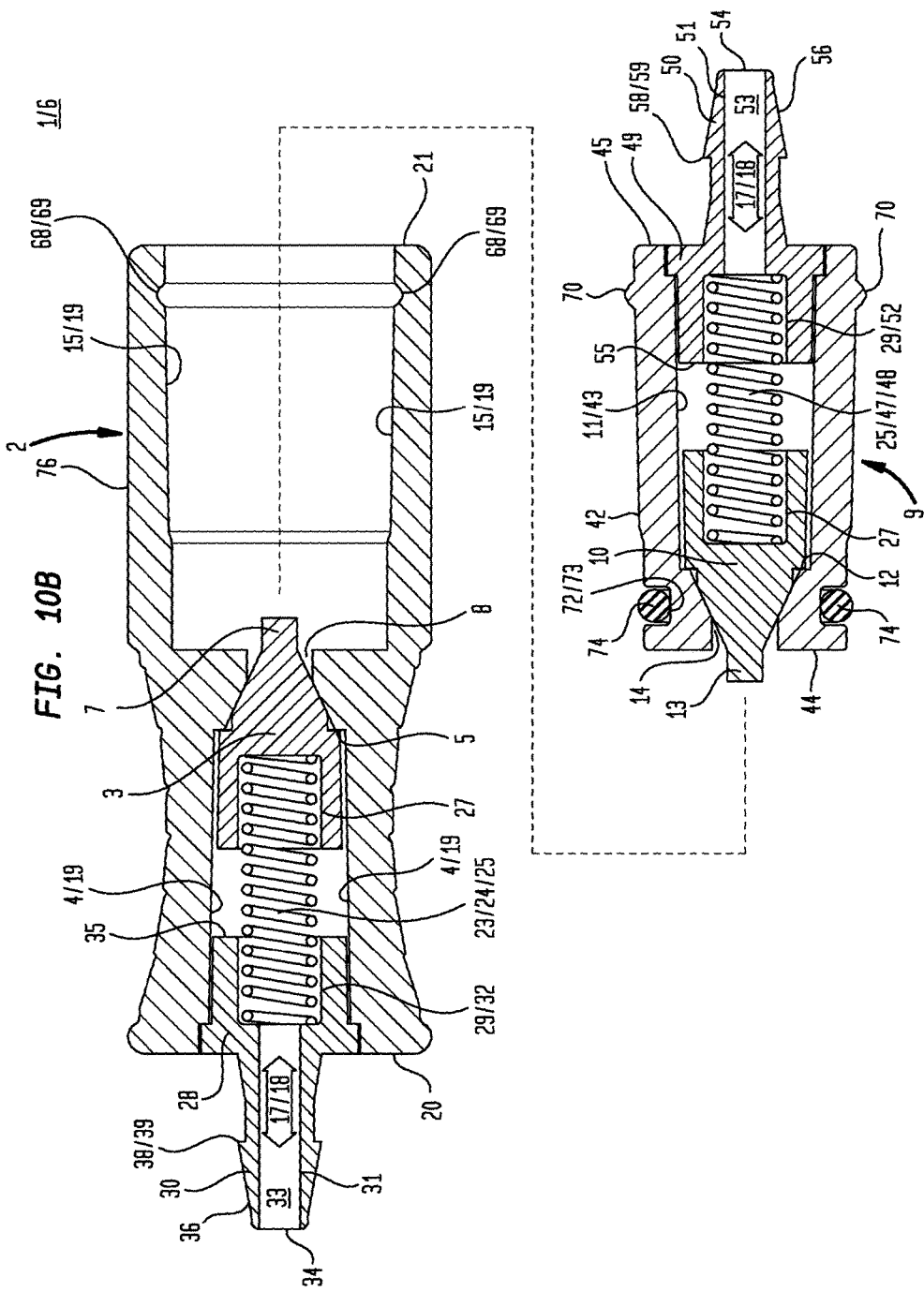
FIG. 10B is an exploded view of the particular embodiment of the inventive coupler shown in FIG. 10A, wherein the first valve element and the second valve element are positioned in a closed position.
Figure 11A:
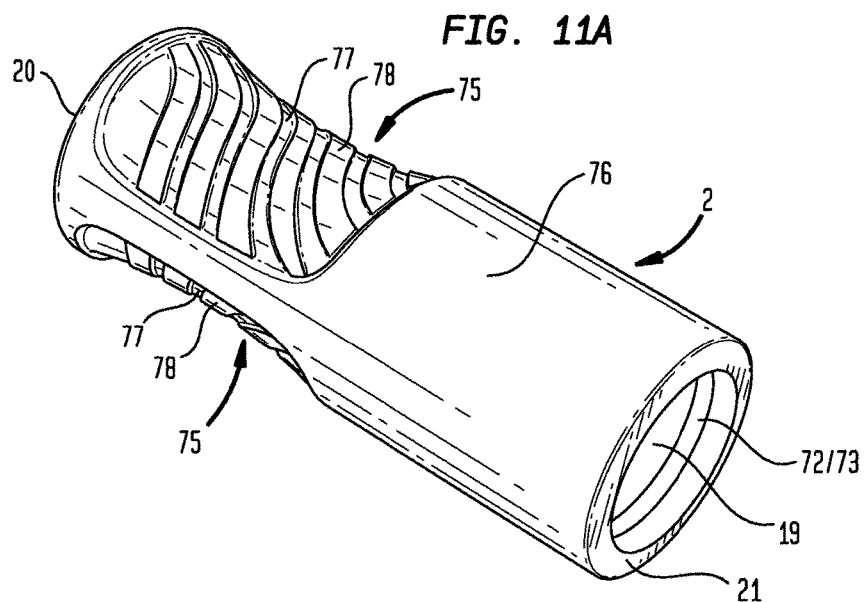
FIG. 11A is a perspective view of a particular embodiment of a coupler body.
Figure 11B:
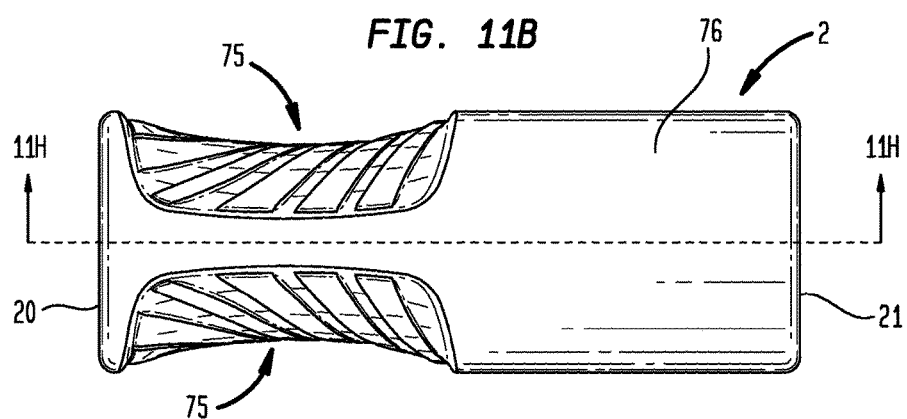
FIG. 11B is a top view of a particular embodiment of a coupler body.
Figure 11C:
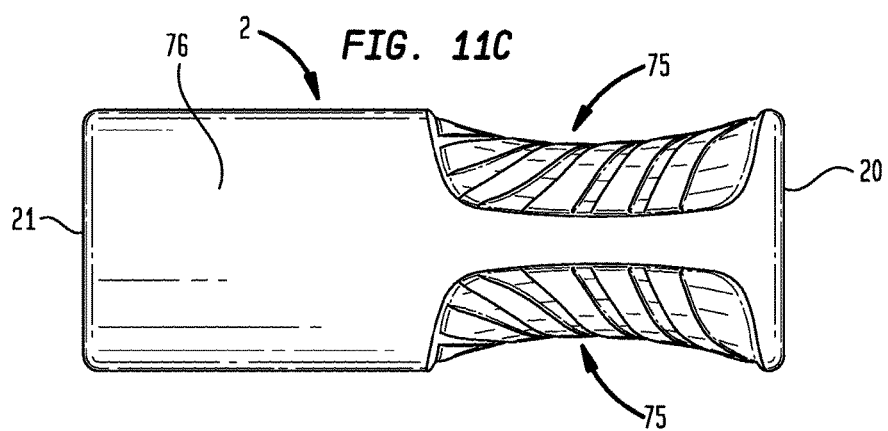
FIG. 11C is a bottom view of a particular embodiment of a coupler body.

Now referring primarily to FIG. 2 through FIG. 12H, the inventive coupler (1) can include a coupler body (2) having a coupler body tubular internal surface (19) which communicates between a coupler body first open end (20) and a coupler body second open end (21) (as shown in the examples of FIG. 10A, FIG. 10B, and FIG. 11H), whereby the coupler body tubular internal surface (19) can define the flow path (18) through the coupler body (2). The coupler body tubular internal surface (19) proximate the coupler body first open end (20) can define a first valve guide (4) coupled to a first valve seat (5) having a first valve port (8), which communicates with a tubular chamber (15) disposed proximate the coupler body second open end (21).

Now referring primarily to FIG. 10A, FIG. 10B, and FIG. 14A through FIG. 14G, the inventive coupler (1) can further include a first valve element (3) having a first valve body (22) coupled to a first valve tip (7). The first valve element (3) can be movable in the first valve guide (4) to sealably engage the first valve seat (5) in a closed position (6), whereby the first valve tip (7) extends through the first valve port (8) a distance into the tubular chamber (15). The first valve element (3) sealably engaged with the first valve seat (5) interrupts the flow path (18) of the coupler body (2) between the coupler body first open end (20) and the coupler body second open end (21).

Again referring primarily to FIG. 10A, FIG. 10B, and FIG. 14A through FIG. 14G, the first valve element (3) can be moved toward the closed position (6) by a first valve actuator (23) disposed adjacent the first valve element (3). The first valve actuator (23) can have any of a numerous and wide variety of configurations capable of moving the first valve element (3) toward the closed position (6). As an illustrative example, the first valve actuator (23) can be configured as a first springing element (24), which can be disposed adjacent the first valve element (3) opposite the first valve tip (7). Accordingly, the first springing element (24) in an extended condition (25) can bias the first valve element (3) toward the tubular chamber (15) to sealably engage the first valve seat (5), thereby positioning the first valve element (3) in the closed position (6) (as shown in the example of FIG. 10B). Forcible urging upon the first valve tip (7) can move the first valve element (3) toward the coupler body first open end (20) disposing the first springing element (24) in a compressed condition (26) which disengages the first valve element (3) from the first valve seat (5), thereby positioning the first valve element (3) toward an open position (16) (as shown in the example of FIG. 10A) to open the flow path (18) through the coupler body (2). As to particular embodiments, the first valve element (3) can further include a first actuator receiving recess (27), which can be disposed opposite the first valve tip (7).

Now referring primarily to FIG. 10A, FIG. 10B, and FIG. 15A through FIG. 15E, a first tubular plug (28) can be coupled to the first valve guide (4) adjacent the first valve actuator (23). As to particular embodiments, the first tubular plug (28) can be fixedly coupled to the first valve guide (4) abuttingly engaging the first springing element (24). The first tubular plug (28) can engage the first springing element (24) to position the first valve element (3) in the closed position (6). As to particular embodiments, the first tubular plug (28) can further include a second actuator receiving recess (29), which can be disposed opposite the first actuator receiving recess (27). The first springing element (24) can be received within the first and second actuator receiving recesses (27)(29) to position the first springing element (24) between the first valve element (3) and the first tubular plug (28).

Again referring primarily to FIG. 10A, FIG. 10B, and FIG. 15A through FIG. 15E, a first tubular member (30) can be coupled to the first tubular plug (28). A first tubular member internal surface (31) and a first tubular plug internal surface (32) can define a first pass-through (33) between a first tubular member first end (34) and a first tubular plug second end (35), the first pass-through (33) communicating with the first valve port (8) when the first tubular plug (28) couples within the first valve guide (4).

A portion of the first tubular member (30) can outwardly extend from the coupler body first open end (20) when the first tubular plug (28) couples within the first valve guide (4). The first tubular member (30) can have a first tubular member external surface (36) configured to join a first conduit (37). As to particular embodiments, the first tubular member external surface (36) can include one or more first annular members (38) extending outwardly from the first tubular member external surface (36), the first annular member (38) forming a first protuberance (39) configured to engage a first conduit internal surface (40) of a first conduit (37) telescopingly engaged about the first tubular member external surface (36). Engagement of the first annular member (38) with the first conduit internal surface (40) can limit travel of the first conduit (37) toward the first tubular member first end (34), thereby maintaining the engagement of the first conduit (37) about the first tubular member (30). As such, a first conduit passage (41) defined by the first conduit internal surface (40) can communicate with the first pass-through (33) as part of the flow path (18) between the first conduit passage (41) and the first valve port (8).

As to particular embodiments, the first tubular member (30) can inwardly taper toward the first tubular member first end (34) to facilitate coupling of the first conduit (37) about the first tubular member (30) via the first tubular member first end (34).

Now referring primarily to FIG. 10A, FIG. 10B, and FIG. 12A through FIG. 12E, the inventive coupler (1) can further include a coupler insert (9) having a coupler insert external surface (42) configured to insert inside of the tubular chamber (15) and a coupler insert tubular internal surface (43) which can communicate as part of the flow path (18) between a coupler insert first open end (44) and a coupler insert second open end (45).

The coupler insert tubular internal surface (19) proximate the coupler insert first open end (44) can define a second valve guide (11) coupled to a second valve seat (12) having a second valve port (14), which can align with the first valve port (8) in substantially coaxial adjacent relation upon insertion of the coupler insert (9) inside of the tubular chamber (15). As such, the first valve port (8) can communicate with the second valve port (14) as part of the flow path (18) between the first conduit passage (41) of the first conduit (37) telescopingly engaged about the first tubular member external surface (36) and the coupler insert second open end (45).

Now referring primarily to FIG. 10A, FIG. 10B, and FIG. 14A through FIG. 14G, the inventive coupler (1) can further include a second valve element (10) having a second valve body (46) coupled to a second valve tip (13). The second valve element (10) can be movable in the second valve guide (11) to sealably engage the second valve seat (12) in a closed position (6), whereby the second valve tip (13) extends through the second valve port (14). The second valve element (10) sealably engaged with the second valve seat (12) interrupts the flow path (18) of the coupler body (2) between the coupler insert first open end (44) and the coupler insert second open end (45).

Again referring primarily to FIG. 10A, FIG. 10B, and FIG. 14A through FIG. 14G, the second valve element (10) can be moved toward the closed position (6) by a second valve actuator (47) disposed adjacent the second valve element (10). The second valve actuator (47) can have any of a numerous and wide variety of configurations capable of moving the second valve element (10) toward a closed position (6). As an illustrative example, the second valve actuator (47) can be configured as a second springing element (48), which can be disposed adjacent the second valve element (10) opposite the second valve tip (13). Accordingly, the second springing element (48) in an extended condition (25) can bias the second valve element (10) toward the coupler insert first open end (44) to sealably engage the second valve seat (12), thereby positioning the second valve element (10) in the closed position (6) (as shown in the example of FIG. 10B). Forcible urging upon the second valve tip (13) can move the second valve element (10) toward the coupler insert second open end (45) disposing the second springing element (48) in a compressed condition (26) which disengages the second valve element (10) from the second valve seat (12), thereby positioning the second valve element (10) toward an open position (16) (as shown in the example of FIG. 10A) to open the flow path (18) through the coupler insert (9). As to particular embodiments, the second valve element (10) can further include a first actuator receiving recess (27), which can be disposed opposite the second valve tip (13).

Now referring primarily to FIG. 10A, FIG. 10B, and FIG. 15A through FIG. 15E, a second tubular plug (49) can be coupled to the second valve guide (11) adjacent the second valve actuator (47). As to particular embodiments, the second tubular plug (49) can be fixedly coupled to the second valve guide (11) abuttingly engaging the second springing element (48). The second tubular plug (49) can engage the second springing element (48) to position the second valve element (10) in the closed position (6). As to particular embodiments, the second tubular plug (49) can further include a second actuator receiving recess (29), which can be disposed opposite the first actuator receiving recess (27). The second springing element (48) can be received within the first and second actuator receiving recesses (27)(29) to position the second springing element (48) between the second valve element (10) and the second tubular plug (49).

Again referring primarily to FIG. 10A, FIG. 10B, and FIG. 15A through FIG. 15E, a second tubular member (50) can be coupled to the second tubular plug (49). A second tubular member internal surface (51) and a second tubular plug internal surface (52) can define a second pass-through (53) between a second tubular member second end (54) and a second tubular plug first end (55), the second pass-through (53) communicating with the second valve port (14) when the second tubular plug (49) couples within the second valve guide (11).

A portion of the second tubular member (50) can outwardly extend from the coupler insert second open end (45) and the coupler body second open end (21) when the second tubular plug (49) couples within the second valve guide (11). The second tubular member (50) can have a second tubular member external surface (56) configured to join a second conduit (57). As to particular embodiments, the second tubular member external surface (56) can include one or more second annular members (58) extending outwardly from the second tubular member external surface (56), the second annular member (58) forming a second protuberance (59) configured to engage a second conduit internal surface (60) of a second conduit (57) telescopingly engaged about the second tubular member external surface (56). Engagement of the second annular member (58) with the second conduit internal surface (60) can limit travel of the second conduit (57) toward the second tubular member second end (54), thereby maintaining the engagement of the second conduit (57) about the second tubular member (50). As such, a second conduit passage (61) defined by the second conduit internal surface (60) can communicate with the second pass-through (53) as part of the flow path (18) between the second conduit passage (61) and the second valve port (14).

As to particular embodiments, the second tubular member (50) can inwardly taper toward the second tubular member second end (54) to facilitate coupling of the second conduit (57) about the second tubular member (50) via the second tubular member second end (54).

Now referring primarily to FIG. 14A through FIG. 14G, the first valve body (22) can further include at least one axial undulation (62) along a first valve body external surface (63). When the first valve element (3) couples within the first valve guide (4), a crest portion (64) of the axial undulation (62) can be disposed adjacent to the coupler body tubular internal surface (19) and a trough portion (65) of the axial undulation (62) can be disposed distal from the coupler body tubular internal surface (19), forming an axial channel (66) between the first valve body external surface (63) and the coupler body tubular internal surface (19). The axial channel (66) can form part of the flow path (18) between the first tubular member first end (34) and the first valve port (8). As to particular embodiments, the first valve body (22) can include a plurality of axial undulations (62) in spaced apart relation, which can provide a plurality of axial channels (66) between the first valve body external surface (63) and the coupler body tubular internal surface (19) (as shown in the example of FIG. 14E).

Again referring primarily to FIG. 14A through FIG. 14G, the second valve body (46) can further include at least one axial undulation (62) along a second valve body external surface (67). When the second valve element (10) couples within the second valve guide (11), a crest portion (64) of the axial undulation (62) can be disposed adjacent to the coupler insert tubular internal surface (43) and a trough portion (65) of the axial undulation (62) can be disposed distal from the coupler insert tubular internal surface (43), forming an axial channel (66) between the second valve body external surface (67) and the coupler insert tubular internal surface (43). The axial channel (66) can form part of the flow path (18) between the second tubular member second end (54) and the second valve port (14). As to particular embodiments, the second valve body (46) can include a plurality of axial undulations (62) in spaced apart relation, which can provide a plurality of axial channels (66) between the second valve body external surface (67) and the coupler insert tubular internal surface (43) (as shown in the example of FIG. 14F).

Now referring primarily to FIG. 10A, FIG. 10B, and FIG. 11H, the coupler body (2) can further include a detent (68) disposed proximate the coupler body tubular internal surface (19). The detent (68) can be configured for releasable fixed axial positioning of the coupler insert (9) inside of the tubular chamber (15). As to particular embodiments, the detent (68) can be configured as an annular groove (69)

disposed in the coupler body tubular internal surface (19) of the tubular chamber (15) proximate the coupler body second open end (21).

Now referring primarily to FIG. 3, FIG. 10A, FIG. 10B, and FIG. 12A through FIG. 13C, the coupler insert (9) can further include at least one radially extending member (70) coupled in circumferentially spaced apart relation about the coupler insert external surface (42). The radially extending member (70) disposed about the coupler insert external surface (42) can be configured to matingly engage with the annular groove (69) to fix an axial position of the coupler insert (9) inside of the tubular chamber (15). As such, a coupler insert (9) can be retained within the tubular chamber (15), thereby engaging the first and second valve tips (7)(13) to position the first and second valve elements (3)(10) in the open position (16) initiating fluid flow (17) through the flow path (18) of the inventive coupler (1). As to particular embodiments, a plurality of radially extending members (70) can be coupled in circumferentially spaced apart relation about the coupler insert external surface (42).

As to particular embodiments, the inventive coupler (1) can further include a plurality of coupler inserts (9) interchangeably insertable into the tubular chamber (15) of the coupler body (2). The one or more radially extending members (70) can be dissimilarly configured between each one of the plurality of coupler inserts (9) to allow selectable retentive arrest of the one or more radially extending members (70) within the annular groove (69). As an illustrative example, the one or more radially extending members (70) can vary in radially extending member height (71) between the plurality of coupler inserts (9) interchangeably insertable into the tubular chamber (15), whereby the selectable retentive arrest can increase with corresponding increase in the radially extending member height (71) (as shown in the example of FIG. 13A through FIG. 13C). Accordingly, a coupler insert (9) having one or more radially extending members (70) with a greater radially extending member height (71) can be retentively retained within the tubular chamber (15) of the coupler body (2) more so than a coupler insert (9) having one or more radially extending members (70) with a lesser radially extending member height (71). As such, the coupler insert (9) having the one or more radially extending members (70) with the greater radially extending member height (71) can require greater separation forces to disengage from the tubular chamber (15) in relation to the coupler insert (9) having the one or more radially extending members (70) with the lesser radially extending member height (71).

Now referring primarily to FIG. 3, FIG. 10A, FIG. 10B, FIG. 12A, FIG. 12B, and FIG. 12E, the inventive coupler (1) can further have a coupler insert seal (72) including an annular recess (73) disposed in the coupler insert external surface (42) proximate the coupler insert first open end (44) and an annular sealing member (74) disposed in the annular recess (73). The annular sealing member (74) can be configured to sealably engage the coupler body tubular internal surface (19) of the tubular chamber (15). When sealably engaged with the coupler body tubular internal surface (19), the annular sealing member (74) can function to further fix the axial position of the coupler insert (9) inside of the tubular chamber (15).

Now referring primarily to a FIG. 2 through FIG. 7, and FIG. 11A through FIG. 11E, the coupler body (2) can further include a gripping surface (75) coupled to a coupler body external surface (76). The gripping surface (75) can include a pair of recess elements (77) disposed in opposed relation in the coupler body external surface (76) proximate the coupler body first open end (20). As to particular embodiments, a plurality raised elements (78) can be disposed in spaced apart relation on each one of the pair of recess elements (77).

A method of producing a particular embodiment of the inventive coupler (1) can include providing a coupler body (2) including a coupler body tubular internal surface (19) which communicates between a coupler body first open end (20) and a coupler body second open end (21), whereby the coupler body tubular internal surface (19) proximate the coupler body first open end (20) defines a first valve guide (4) coupled to a first valve seat (5) having a first valve port (8), the first valve port (8) communicating with a tubular chamber (15) disposed proximate the coupler body second open end (21).

The method can further include coupling a first valve element (3) to the first valve guide (4), the first valve element (3) having a first valve body (22) coupled to a first valve tip (7). The first valve element (3) can be movable in the first valve guide (4) to sealably engage the first valve seat (5) in a closed position (6) with the first valve tip (7) extending through the first valve port (8) a distance into the tubular chamber (15). The method can further include disposing a first valve actuator (23) adjacent the first valve element (3) to facilitate movement of the first valve element (3) toward the closed position (6).

The method can further include coupling a first tubular plug (28) to the first valve guide (4) adjacent the first valve actuator and coupling a first tubular member (30) to the first tubular plug (28), the first tubular member (30) having a first tubular member external surface (36) configured to join a first conduit (37).

The method can further include providing a coupler insert (9) including a coupler insert external surface (42) configured to insert inside of the tubular chamber (15) and a coupler insert tubular internal surface (43) which communicates between a coupler insert first open end (44) and a coupler insert second open end (45), the coupler insert tubular internal surface (19) defining a second valve guide (11) coupled to a second valve seat (12) having a second valve port (14), the second valve port (14) aligned with the first valve port (8) upon insertion of the coupler insert (9) inside of the tubular chamber (15).

The method can further include coupling a second valve element (10) to the second valve guide (11), the second valve element (10) having a second valve body (46) coupled to a second valve tip (13). The second valve element (10) can be movable in the second valve guide (11) to sealably engage the second valve seat (12) in a closed position (6) with the second valve tip (13) extending through the second valve port (14). The method can further include disposing a second valve actuator (47) adjacent the second valve element (10) to facilitate movement of the second valve element (10) toward the closed position (6).

The method can further include coupling a second tubular plug (49) to the second valve guide (11) adjacent the second valve actuator (47) and coupling a second tubular member (50) to the second tubular plug (49), the second tubular member (50) having a second tubular member external surface (56) configured to join a second conduit (57).

The first valve tip (7) can engage the second valve tip (13) upon insertion of the coupler insert (9) inside of the tubular chamber (15), whereby the first valve element (3) disengages the first valve seat (5) and the second valve element (10) disengages the second valve seat (12) to open a flow path (18) through the inventive coupler (1).

As to particular embodiments, the method can further include configuring at least one axial undulation (62) along a first valve body external surface (63) of the first valve body (22).

As to particular embodiments, the method can further include configuring at least one axial undulation (62) along a second valve body external surface (67) of the second valve body (46).

As to particular embodiments, the method can further include disposing a detent (68) proximate the coupler body tubular internal surface (19) of the coupler body (2), the detent (68) configured for releasable fixed axial positioning of the coupler insert (9) inside of the tubular chamber (15).

As to particular embodiments, the method can further include configuring the detent (68) as an annular groove (69) and disposing the annular groove (69) in the coupler body tubular internal surface (19) of the tubular chamber (15) proximate the coupler body second open end (21).

As to particular embodiments, the method can further include coupling at least one radially extending member (70) about the coupler insert external surface (42) of the coupler insert (9), the radially extending member (70) configured to matingly engage with the annular groove (69) to fix an axial position of the coupler insert (9) inside of the tubular chamber (15).

As to particular embodiments, the method can further include providing a plurality of coupler inserts (9) interchangeably insertable into the tubular chamber (15) of the coupler body (2), the at least one radially extending member (70) dissimilarly configured between each one of the plurality of coupler inserts (9) to allow selectable retentive arrest of the at least one radially extending member (70) within the annular groove (69). As to particular embodiments, the at least one radially extending member (70) can vary in radially extending member height (71) between the plurality of coupler inserts (9) interchangeably insertable into the tubular chamber (15), the selectable retentive arrest increasing with corresponding increase in the radially extending member height (71).

As to particular embodiments, the method can further include providing a coupler insert seal (72) including an annular recess (73) disposed in the coupler insert external surface (42) proximate the coupler insert first open end (20) and an annular sealing member (74) disposed in the annular recess (73), the annular sealing member (74) configured to sealably engage the coupler body tubular internal surface (19) of the tubular chamber (15).

As to particular embodiments, the method can further include coupling a gripping surface (75) to a coupler body external surface (76) of the coupler body (2), the gripping surface (75) including a pair of recess elements (77) disposed in opposed relation in the coupler body external surface (76) proximate the coupler body first open end (20) and a plurality raised elements (78) disposed in spaced apart relation on each one of the pair of recess elements (77).

As to particular embodiments, elements of the inventive coupler (1) can be entirely formed of the same material, or alternatively, various elements of the inventive coupler (1) can be formed from different materials. The inventive coupler (1) or elements of the inventive coupler (1) can be produced from any of a wide variety of materials, including substantially inflexible materials, resiliently flexible materials, resiliently deformable materials, or the like, or combinations thereof. By way of non-limiting example, the material can include or consist of: rubber, rubber-like material, plastic, plastic-like material, acrylic, polyamide, polyester, polypropylene, polyethylene, polyvinyl chloride-based materials, silicone-based materials, or the like, or combinations thereof. Additional non-limiting examples can include polymeric materials or resins, for example thermoplastics, such as acrylic, nylon, polybenzimidazole, polyethylene, polypropylene, polystyrene, polyvinyl chloride, polytetrafluoroethylene, or the like, or combinations thereof; thermosets, such as polyester fiberglass, polyurethanes, rubber, polyoxybenzylmethylenglycolanhydride, urea-formaldehyde foam, melamine resin, epoxy resin, polyimides, cynate esters, polycyanurates, polyester resin, or the like, or combinations thereof; elastomers, such as natural polyisoprene, synthetic polyisoprene, polybutadiene, chloropene rubber, butyl rubber, styrene-butadiene rubber, nitrile rubber, ethylene propylene rubber, epichlorohydrin rubber, polyacrylic rubber, silicone rubber, fluorosilicone rubber, fluoroelastomers, perfluoroelastomers, polyether block amides, chlorosulfonated polyethylene, ethylene-vinyl acetate, thermal plastic elastomer (TPE), or the like, or combinations thereof.

As to particular embodiments, the inventive coupler (1) or elements of the inventive coupler (1) can be produced from any of a wide variety of processes depending upon the application, such as press molding, injection molding, fabrication, machining, printing, three-dimensional printing, or the like, or combinations thereof, as one piece or assembled from a plurality of pieces into an embodiment of the inventive coupler (1) or provided as a plurality of pieces for assembly into an embodiment of the inventive coupler (1).

A method of using a particular embodiment of the inventive coupler (1) can include obtaining an inventive coupler (1) having elements as described above, inserting the coupler insert (9) inside of the tubular chamber (15), engaging the first valve tip (7) with the second valve tip (13), and disengaging the first valve element (3) from the first valve seat (5) and disengaging the second valve element (10) from the second valve seat (12) to open a flow path (18) through the inventive coupler (1).

Now referring primarily to FIG. 1A and FIG. 10A, as to particular embodiments having a first conduit (37) telescopingly engaged about the first tubular member external surface (36) and a second conduit (57) telescopingly engaged about the second tubular member external surface (56), fluid can flow through the inventive coupler (1) by ingressing from the first conduit passage (41) of the first conduit (37) to the first pass-through (33), flowing through the first valve guide (4) coupled to the first valve seat (5), the first valve port (8), the second valve port (14), the second valve guide (11) coupled to the second valve seat (5), and the second pass-through (53), egressing from the second tubular member second end (54) to the second conduit passage (61) of the second conduit (57). As to other particular embodiments, fluid can flow through the inventive coupler (1) by ingressing from the second conduit passage (61) of the second conduit (57) to the second pass-through (53), flowing through the second valve guide (11) coupled to the second valve seat (12), the second valve port (14), the first valve port (8), the first valve guide (4) coupled to the first valve seat (5), and the first pass-through (33), egressing from the first tubular member first end (34) to the first conduit passage (41) of the first conduit (37). As such, the inventive coupler (1) can fluidicly couple the first and second conduit passages (41)(61).

The method can further include moving the coupler body (2) and the coupler insert (9) in outward opposed axial directions, disengaging the first valve tip (7) and the second valve tip (13), and engaging the first valve element (3) with the first valve seat (5) and engaging the second valve element (10) with the second valve seat (12) to close the flow path (18) through the inventive coupler (1). As such, the fluid flow (17) through the inventive coupler (1) can be interrupted by the first and second valve elements (3)(10). Correspondingly, the fluid flow (17) between the first and second conduits (37)(57) can be interrupted without a substantial loss of fluid from the first and second conduit passages (41)(61).

As can be easily understood from the foregoing, the basic concepts of the present invention may be embodied in a variety of ways. The invention involves numerous and varied embodiments of a releasable valved coupler and methods for making and using such releasable valved couplers including the best mode.

As such, the particular embodiments or elements of the invention disclosed by the description or shown in the figures or tables accompanying this application are not intended to be limiting, but rather exemplary of the numerous and varied embodiments generically encompassed by the invention or equivalents encompassed with respect to any particular element thereof. In addition, the specific description of a single embodiment or element of the invention may not explicitly describe all embodiments or elements possible; many alternatives are implicitly disclosed by the description and figures.

It should be understood that each element of an apparatus or each step of a method may be described by an apparatus term or method term. Such terms can be substituted where desired to make explicit the implicitly broad coverage to which this invention is entitled. As but one example, it should be understood that all steps of a method may be disclosed as an action, a means for taking that action, or as an element which causes that action. Similarly, each element of an apparatus may be disclosed as the physical element or the action which that physical element facilitates. As but one example, the disclosure of a "coupler" should be understood to encompass disclosure of the act of "coupling"—whether explicitly discussed or not—and, conversely, were there effectively disclosure of the act of "coupling", such a disclosure should be understood to encompass disclosure of a "coupler" and even a "means for coupling." Such alternative terms for each element or step are to be understood to be explicitly included in the description.

In addition, as to each term used it should be understood that unless its utilization in this application is inconsistent with such interpretation, common dictionary definitions should be understood to included in the description for each term as contained in the Random House Webster's Unabridged Dictionary, second edition, each definition hereby incorporated by reference.

All numeric values herein are assumed to be modified by the term "about", whether or not explicitly indicated. For the purposes of the present invention, ranges may be expressed as from "about" one particular value to "about" another particular value. When such a range is expressed, another embodiment includes from the one particular value to the other particular value. The recitation of numerical ranges by endpoints includes all the numeric values subsumed within that range. A numerical range of one to five includes for example the numeric values 1, 1.5, 2, 2.75, 3, 3.80, 4, 5, and so forth. It will be further understood that the endpoints of each of the ranges are significant both in relation to the other endpoint, and independently of the other endpoint. When a value is expressed as an approximation by use of the antecedent "about," it will be understood that the particular value forms another embodiment. The term "about" generally refers to a range of numeric values that one of skill in the art would consider equivalent to the recited numeric value or having the same function or result. Similarly, the antecedent "substantially" means largely, but not wholly, the same form, manner or degree and the particular element will have a range of configurations as a person of ordinary skill in the art would consider as having the same function or result. When a particular element is expressed as an approximation by use of the antecedent "substantially," it will be understood that the particular element forms another embodiment.

Moreover, for the purposes of the present invention, the term "a" or "an" entity refers to one or more of that entity unless otherwise limited. As such, the terms "a" or "an", "one or more" and "at least one" can be used interchangeably herein.

Thus, the applicant(s) should be understood to claim at least: i) each of the releasable valved couplers herein disclosed and described, ii) the related methods disclosed and described, iii) similar, equivalent, and even implicit variations of each of these devices and methods, iv) those alternative embodiments which accomplish each of the functions shown, disclosed, or described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced by such systems or components, ix) methods and apparatuses substantially as described hereinbefore and with reference to any of the accompanying examples, x) the various combinations and permutations of each of the previous elements disclosed.

The background section of this patent application provides a statement of the field of endeavor to which the invention pertains. This section may also incorporate or contain paraphrasing of certain United States patents, patent applications, publications, or subject matter of the claimed invention useful in relating information, problems, or concerns about the state of technology to which the invention is drawn toward. It is not intended that any United States patent, patent application, publication, statement or other information cited or incorporated herein be interpreted, construed or deemed to be admitted as prior art with respect to the invention.

The claims set forth in this specification, if any, are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice-versa as necessary to define the matter for which protection is sought by this application or by any subsequent application or continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

Additionally, the claims set forth in this specification, if any, are further intended to describe the metes and bounds of a limited number of the preferred embodiments of the invention and are not to be construed as the broadest embodiment of the invention or a complete listing of embodiments of the invention that may be claimed. The applicant does not waive any right to develop further claims based upon the description set forth above as a part of any continuation, division, or continuation-in-part, or similar application.

The invention claimed is:

1. A coupler, comprising:
   a coupler body including:
   a coupler body internal surface which communicates between a coupler body first open end and a coupler body second open end, said coupler body internal surface proximate said coupler body second open end defining a tubular chamber;
   an annular groove disposed in said coupler body internal surface of said tubular chamber;
   a coupler insert including:
   a coupler insert external surface insertable inside of said tubular chamber; and
   a plurality of radially extending members disposed in circumferentially spaced apart relation about said coupler insert external surface, said plurality of radially extending members disposable in said annular groove to allow releasable retentive arrest of said coupler insert inside of said tubular chamber.

2. The coupler of claim 1, further comprising a plurality of coupler inserts interchangeably insertable into said tubular chamber of said coupler body, said plurality radially extending members dissimilarly configured between each one of said plurality of coupler inserts to allow selectable retentive arrest of said plurality of radially extending members within said annular groove.

3. The coupler of claim 2, wherein said plurality of radial extending members vary in member height between said plurality of coupler inserts interchangeably insertable into said tubular chamber, said selectable retentive arrest increasing with corresponding increase in said member height.

4. The coupler of claim 1, wherein said coupler body tubular internal surface proximate said coupler body first open end defines a first valve guide coupled to a first valve seat having a first valve port which communicates with said tubular chamber disposed proximate said coupler body second open end; and
   a first valve element having a first valve body, said first valve element movable in said first valve guide to sealably engage said first valve seat in a closed position.

5. The coupler of claim 4, wherein a coupler insert internal surface defines a second valve guide coupled to a second valve seat having a second valve port, said second valve port aligned with said first valve port upon insertion of said coupler insert inside of said tubular chamber; and
   a second valve element having a second valve body, said second valve element movable in said second valve guide to sealably engage said second valve seat in a closed position.

6. The coupler of claim 5, further comprising:
   a first valve tip coupled to said first valve body, said first valve tip extending through said first valve port a distance into said tubular chamber in said closed position of said first valve body; and
   a second valve tip coupled to said second valve body, said second valve tip extending through said second valve port in said closed position of second valve body, wherein said first valve tip engages said second valve tip upon insertion of said coupler insert inside of said tubular chamber, whereby said first valve element disengages said first valve seat and said second valve element disengages said second valve seat to open a flow path through said coupler.

7. The coupler of claim 6, further comprising:
   a first valve actuator adjacent said first valve element to facilitate movement of said first valve element toward said closed position; and
   a second valve actuator adjacent said second valve element to facilitate movement of said second valve element toward said closed position.

8. The coupler of claim 6, further comprising at least one axial undulation along a first valve body external surface of said first valve body.

9. The coupler of claim 8, further comprising at least one axial undulation along a second valve body external surface of said second valve body.

10. The coupler of claim 1, further comprising a coupler insert seal including:
    an annular recess disposed in said coupler insert external surface proximate said coupler insert first open end; and
    an annular sealing member disposed in said annular recess, said annular sealing member configured to sealably engage said coupler body internal surface of said tubular chamber.

11. The coupler of claim 1, wherein said coupler body further comprises a gripping surface coupled to a coupler body external surface, said gripping surface including:
    a pair of recess elements disposed in opposed relation in said coupler body external surface proximate said coupler body first open end; and
    a plurality of raised elements disposed in spaced apart relation on each one of said pair of recess elements.

12. A method of producing a coupler, comprising:
    configuring a coupler body, including:
    a coupler body internal surface which communicates between a coupler body first open end and a coupler body second open end, said coupler body internal surface proximate said coupler body second open end defining a tubular chamber;
    an annular groove disposed in said coupler body internal surface of said tubular chamber;
    configuring a coupler insert, including:
    a coupler insert external surface insertable inside of said tubular chamber; and
    a plurality of radially extending members disposed in circumferentially spaced apart relation about said coupler insert external surface, said plurality of radially extending members disposable in said annular groove to allow releasable retentive arrest of said coupler insert inside of said tubular chamber.

13. The method of claim 12, further comprising configuring a plurality of coupler inserts interchangeably insertable into said tubular chamber of said coupler body, said plurality radially extending members dissimilarly configured between each one of said plurality of coupler inserts to allow selectable retentive arrest of said plurality of radially extending members within said annular groove.

14. The method of claim 13, further comprising varying member height of said plurality of radial extending members between said plurality of coupler inserts interchangeably insertable into said tubular chamber, said selectable retentive arrest increasing with corresponding increase in said member height.

15. The method of claim 12, further comprising configuring said a coupler body internal surface proximate said coupler body first open end to define a first valve guide coupled to a first valve seat having a first valve port which communicates with said tubular chamber disposed proximate said coupler body second open end; and movably disposing a first valve body in said first valve guide to sealably engage said first valve seat in a closed position.

16. The method of claim 15, further comprising configuring said coupler insert internal surface to define a second valve guide coupled to a second valve seat having a second valve port, said second valve port aligned with said first valve port upon insertion of said coupler insert inside of said tubular chamber; and movably disposing a second valve body in said second valve guide to sealably engage said second valve seat in a closed position.

17. The method of claim 16, further comprising:
coupling a first valve tip to said first valve body, said first valve tip extending through said first valve port a distance into said tubular chamber in said closed position of said first valve body; and
coupling a second valve tip coupled to said second valve body, said second valve tip extending through said second valve port in said closed position of second valve body,
wherein said first valve tip engages said second valve tip upon insertion of said coupler insert inside of said tubular chamber, whereby said first valve element disengages said first valve seat and said second valve element disengages said second valve seat to open a flow path through said coupler.

18. The method of claim 17, further comprising:
disposing a first valve actuator adjacent said first valve element to facilitate movement of said first valve element toward said closed position; and
disposing a second valve actuator adjacent said second valve element to facilitate movement of said second valve element toward said closed position.

19. The method of claim 16, further comprising disposing at least one axial undulation along a first valve body external surface of said first valve body.

20. The method of claim 19, further comprising at least one axial undulation along a second valve body external surface of said second valve body.

21. The method of claim 12, further comprising a coupler insert seal including:
disposing an annular recess in said coupler insert external surface proximate said coupler insert first open end; and
disposing an annular sealing member in said annular recess, said annular sealing member configured to sealably engage said coupler body internal surface of said tubular chamber.

22. The method of claim 12, further comprising coupling a gripping surface to a coupler body external surface, said gripping surface including:
a pair of recess elements disposed in opposed relation in said coupler body external surface proximate said coupler body first open end; and
a plurality of raised elements disposed in spaced apart relation on each one of said pair of recess elements.

23. A method of using a coupler, the method comprising:
obtaining a coupler body, including:
a coupler body internal surface which communicates between a coupler body first open end and a coupler body second open end, said coupler body internal surface proximate said coupler body second open end defining a tubular chamber;
an annular groove disposed in said coupler body internal surface of said tubular chamber;
obtaining a coupler insert, including:
a coupler insert external surface insertable inside of said tubular chamber; and
a plurality of radially extending members disposed in circumferentially spaced apart relation about said coupler insert external surface,
inserting said coupler insert into said tubular chamber of said coupler body; and
disposing said plurality of radially extending members in said annular groove allowing releasable retentive arrest of said coupler insert inside of said tubular chamber.

24. The method of claim 23, further comprising:
moving said coupler body and said coupler insert in outward opposed axial directions;
disengaging said plurality of radially extending members from said groove; and
removing said coupler insert from inside of said tubular chamber.

25. The method of claim 24, further comprising:
disengaging said first valve tip and said second valve tip; and
engaging said first valve element with said first valve seat and engaging said second valve element with said second valve seat to close said flow path through said coupler.

26. The method of claim 23,
wherein a coupler body internal surface proximate said coupler body first open end further including:
a first valve guide coupled to a first valve seat having a first valve port, said first valve port communicating with a tubular chamber disposed proximate said coupler body second open end; and
a first valve element having a first valve body coupled to a first valve tip, said first valve element movable in said first valve guide to sealably engage said first valve seat in a closed position with said first valve tip extending through said first valve port a distance into said tubular chamber, and
wherein said coupler insert internal surface further includes:
a second valve guide coupled to a second valve seat having a second valve port, said second valve port aligned with said first valve port upon insertion of said coupler insert inside of said tubular chamber;
a second valve element having a second valve body coupled to a second valve tip, said second valve element movable in said second valve guide to sealably engage said second valve seat in a closed position with said second valve tip extending through said second valve port;
engaging said first valve tip with said second valve tip; and
disengaging said first valve element from said first valve seat and disengaging said second valve element from said second valve seat to open a flow path through said coupler.

* * * * *